(12) United States Patent
Ray, II

(10) Patent No.: US 12,156,875 B2
(45) Date of Patent: *Dec. 3, 2024

(54) WOUND TREATMENTS AND COMPOSITIONS

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/513,737

(22) Filed: Oct. 28, 2021

(65) Prior Publication Data

US 2022/0047590 A1 Feb. 17, 2022

Related U.S. Application Data

(63) Continuation-in-part of application No. 16/381,975, filed on Apr. 11, 2019.

(51) Int. Cl.
| | |
|---|---|
| *A61K 31/505* | (2006.01) |
| *A61K 9/00* | (2006.01) |
| *A61K 9/06* | (2006.01) |
| *A61K 9/14* | (2006.01) |
| *A61K 31/366* | (2006.01) |
| *A61K 31/40* | (2006.01) |
| *A61K 31/405* | (2006.01) |
| *A61K 31/47* | (2006.01) |
| *A61K 31/485* | (2006.01) |

(52) U.S. Cl.
CPC .......... *A61K 31/505* (2013.01); *A61K 9/0014* (2013.01); *A61K 9/06* (2013.01); *A61K 31/366* (2013.01); *A61K 31/40* (2013.01); *A61K 31/405* (2013.01); *A61K 31/47* (2013.01); *A61K 31/485* (2013.01)

(58) Field of Classification Search
CPC ...... A61K 31/505; A61K 9/0014; A61K 9/06; A61K 31/366; A61K 31/40; A61K 31/405; A61K 31/47; A61K 31/485

See application file for complete search history.

(56) References Cited

U.S. PATENT DOCUMENTS

| | | | | |
|---|---|---|---|---|
| 6,558,710 | B1 * | 5/2003 | Godfrey | A61K 33/30 424/641 |
| 7,517,852 | B2 * | 4/2009 | Walsh | A61K 31/7036 514/2.9 |
| 2003/0190300 | A1 * | 10/2003 | Scancarella | A61Q 19/08 424/778 |
| 2004/0087630 | A1 | 5/2004 | Allison | |
| 2007/0203209 | A1 * | 8/2007 | Bartolini | C07D 209/18 514/367 |
| 2011/0052704 | A1 | 3/2011 | Nazzal | |
| 2011/0105996 | A1 * | 5/2011 | Mustoe | A61K 9/0019 424/754 |
| 2011/0245786 | A1 | 10/2011 | Hulse | |
| 2014/0171460 | A1 * | 6/2014 | Zagon | A61K 9/70 514/282 |
| 2017/0096418 | A1 * | 4/2017 | Patron | A23L 2/52 |
| 2020/0113899 | A1 | 4/2020 | Chase | |

* cited by examiner

*Primary Examiner* — Savitha M Rao
*Assistant Examiner* — Andrew P Lee
(74) *Attorney, Agent, or Firm* — AKERMAN LLP

(57) ABSTRACT

A method of treating a wound may include topically administering a statin composition including a statin selected from atorvastatin, fluvastatin, lovastatin, pitavastatin, pravastatin, rosuvastatin, simvastatin, or combination thereof. The statin composition may be administered in an ointment, powder, or liquid format. The method may also include topically administering one or more antimicrobial drugs and/or naltrexone.

8 Claims, No Drawings

WOUND TREATMENTS AND COMPOSITIONS

CROSS-REFERENCE TO RELATED APPLICATIONS

The present application is a continuation-in-part of U.S. patent application Ser. No. 16/381,975, filed Apr. 11, 2019, the contents of which are hereby incorporated herein by reference.

TECHNICAL FIELD

The present application relates to compounded wound treatments and methods of treating wounds. More specifically, the present application relates to topical compounded wound treatments including one or more statins and methods of topically treating wounds with the same.

BACKGROUND

Wound healing is a complex and dynamic process in which tissues repair from damage. The process generally includes a hemostasis phase, an inflammation phase, a granulation tissue formation phase, and a tissue remodeling phase. Wounds may occur from broken or unbroken skin as a result of blunt trauma, punctures, excessive exposure to cold or heat, chemical exposure, radiation exposure, and surgical procedures. Wounds may also arise as itching, scaling, swelling, or blistering of the skin. Wounds may also arise from eczemas, chronic skin conditions such as psoriasis, rosacea, and conditions accompanying bacterial, viral, or fungal infections may also damage skin.

Many factors can complicate or interfere with normal adequate wound healing. For example, such factors include age, infection, poor nutrition, immunosuppression, medications, radiation, diabetes, peripheral vascular disease, systemic illness, smoking, or stress. Abnormal wound healing can increase susceptibility to local infection, which also increases the risk systemic infection. What is needed are additional and alternative wound healing compositions for the treatment of wounds.

SUMMARY

In one aspect, a method of formulating a topical wound treatment composition includes mixing dry powder contents of a pharmaceutical container with petrolatum, a water-washable-ointment, or a cream type vehicle, wherein the dry powder contents comprise 5 mg to 200 mg of one or more statins.

In one example, the one or more statins are selected from atorvastatin, fluvastatin, lovastatin, pitavastatin, pravastatin, rosuvastatin or simvastatin.

In one example, the dry powder contents further comprise between 1 mg and 50 mg naltrexone.

In one example, the dry powder contents further comprise an antibiotic drug or an antifungal drug.

In one example, the dry powder contents further comprise between 1 mg and 50 mg naltrexone and an antibiotic drug or an antifungal drug.

In one example, the topical composition includes the water-washable-ointment, and the water-washable-ointment comprises PEG-8, PEG-75, meadowsweet extract, zinc acetate, and propylene glycol.

In one example, the dry powder contents further comprise xylitol or poloxamers. The dry powder contents further comprise between 1 mg and 50 mg naltrexone and/or at least one of an antibiotic drug or an antifungal drug.

In one example, the dry powder contents of the pharmaceutical container are mixed with one or more additional dry powder active or inactive ingredients. The mixing may include using a motorized shaker-type mixer.

In one example, dry powder of the one more statins are mixed with one or more additional dry powder active or inactive ingredients and the pharmaceutical container including the dry powder is generated by supplying the dry powders into the pharmaceutical container. Mixing the dry powders may include using a motorized shaker-type mixer.

In one example, the pharmaceutical container comprises a capsule, satchel, powder pack, or other suitable container for containing pharmaceutical dry powders.

In another aspect, a method of treating a wound includes administering a topical composition formulated by mixing dry powder contents of a pharmaceutical container comprising 5 mg to 200 mg of one or more statins with petrolatum, a water-washable-ointment, or a cream type vehicle to a target tissue comprising a wound.

In one example, the pharmaceutical container comprises a capsule, satchel, powder pack, or other suitable container for containing pharmaceutical dry powders.

In one example, the one or more statins are selected from atorvastatin, fluvastatin, lovastatin, pitavastatin, pravastatin, rosuvastatin or simvastatin.

In one example, the topical composition further comprises between 1 mg and 50 mg naltrexone.

In one example, the topical composition further comprises an antibiotic drug or an antifungal drug.

In one example, the topical composition further comprises between 1 mg and 50 mg naltrexone and an antibiotic drug or an antifungal drug. The topical composition may include the water-washable-ointment, and the water-washable-ointment may include PEG-8, PEG-75, meadowsweet extract, zinc acetate, and propylene glycol.

In one example, the topical composition further includes xylitol or poloxamers. The dry powder contents further comprise between 1 mg and 50 mg naltrexone and/or at least one of an antibiotic drug or an antifungal drug.

In one example, bacterial, fungal, or other causative organisms are present on the target tissue.

In one example, bacterial, fungal, or other causative organisms are not present on the target tissue.

In yet another aspect, a method of treating a wound includes administering dry powder contents of a pharmaceutical container to target tissue comprising a wound, wherein the dry powder contents comprise between 5 mg and 200 mg of one or more statins.

In one example, the pharmaceutical container comprises a capsule, satchel, powder pack, or other suitable container for containing pharmaceutical dry powders.

In one example, the one or more statins are selected from atorvastatin, fluvastatin, lovastatin, pitavastatin, pravastatin, rosuvastatin or simvastatin.

In one example, the dry powder contents further comprise between 1 mg and 50 mg naltrexone.

In one example, the dry powder contents further comprise an antibiotic drug or an antifungal drug.

In one example, the dry powder contents further comprise between 1 mg and 50 mg naltrexone and an antibiotic drug or an antifungal drug.

In one example, the dry powder contents further comprise xylitol or poloxamers. The dry powder contents may further include between 1 mg and 50 mg naltrexone and/or at least one of an antibiotic drug or an antifungal drug.

In one example, bacterial, fungal, or other causative organisms are present on the target tissue.

In one example, bacterial, fungal, or other causative organisms are not present on the target tissue.

DESCRIPTION

In various embodiments, a topical treatment includes a topical statin component comprising one or more statins and an additional active component comprising one or more additional active drugs such as antimicrobial or collagenase. In various embodiments, a topical treatment includes collagenase alone or together with one or more statins, one or more antimicrobials, naltrexone, additional actives or inactives, or combinations thereof. The active drugs identified herein may include pharmaceutically acceptable salts and derivatives of the identified active drugs. In some embodiments, a topical treatment includes a topical statin component comprising one or more statins without an additional active component.

The topical treatment may comprise one or more topical compositions comprising the statin component and additional active component, when present, for co-administration. For example, the topical treatment may include a topical composition containing all or a portion of the statin component in a powder, ointment, spray solution, irrigation solution, or footbath solution format. A solution may include dissolved, suspended, or dispersed solute. The composition may comprise a contained or contained powder, premix composition, or a composition for administration, any of which may be provided in a single or multi-dose format. One or more base components may be included in the composition as a contained powder, premix composition, or composition for administration. The topical composition containing statin component may include all or a portion of an additional active component or the additional active component may be present in a separate topical composition, which may be provided in a powder, cream, lotion, ointment, irrigation/bath solution, emulsion o/w or w/o, gel, or paste format, for example. In some embodiments, the topical treatment may comprise a single topical composition comprising the statin component without an additional active component or multiple topical compositions comprising the statin component without an additional active component. In various embodiments, a topical treatment includes collagenase alone or together with one or more statins, one or more antimicrobials, naltrexone, one or more additional actives or inactives, or combinations thereof. The topical composition containing collagenase may include all or a portion of an additional active component or the additional active component may be present in a separate topical composition, which may be provided in a powder, cream, lotion, ointment, irrigation/bath solution, emulsion o/w or w/o, gel, or paste format, for example.

As introduced above, in various embodiments, the topical treatment comprises a pharmaceutical container comprising one or more statin powders as described herein. Additional powders may also be included, such as an antimicrobial drug powder comprising one or more antimicrobial drugs, collagenase powder, naltrexone powder, various additional active agents, base component powder, and/or others described herein. Additional powders may be included, such as one or more antimicrobial drugs, naltrexone powder, various additional active agents, base component powder, and/or other active agents described herein. In one example, the contained, e.g., contained, powder may be formulated for topical administration to a wound, necrotic tissue, broken tissue, unbroken tissue, or other targeted areas of the body, that may or may not be infected, and thus may comprise a topical composition for administration that may be removed from the pharmaceutical container and applied to the target tissue. In another example, the contained powder may be formulated for addition to one or more base components to formulate a compounded premix composition or a composition for administration. Co-administration compositions may comprise same or different formats. One or more co-administration compositions may be provided as contained powders, administration compositions, or premix compositions, for example. In some embodiments, topical compositions for co-administration include a statin component containing topical composition described herein and an additional active component containing topical composition described herein, such as one or more antimicrobial, collagenase, naltrexone, and/or other active agent containing composition. In another example, the topical compositions for co-administration include a collagenase containing topical composition that may include or be co-administered with one or more antimicrobial drugs, naltrexone powder, various additional active agents, base component powder, and/or other active agents described herein. The compositions may comprise a contained powder, ground tablets, solution, ointment, lotion, cream, paste, or gel, for example. One or more of the compositions may be provided as premix compositions or administration compositions. The compositions may be combined or co-administered separately. In various embodiments, the pharmaceutical container comprises a capsule, satchel, powder pack, or other suitable container for containing pharmaceutical dry powders. In some examples, a method of treating a body surface or wound thereof or formulating a composition for the same may include adding dry powder including active ingredients into the pharmaceutical container. In some embodiments, one or more dry powders including inactive may similarly be supplied into the pharmaceutical container. In one embodiment, a method may include mixing a plurality of dry powder actives and supplying them into the pharmaceutical container. In a further embodiment, the method may include mixing a plurality of dry power active and inactive ingredients and supplying them into the pharmaceutical container.

In various embodiments, a base component may comprise one or more carriers, diluents, solubilizers, stabilizers (which may include antioxidants), buffers, tonicity modifiers, bulking agents, viscosity modifiers (enhancers/reducers), surfactants, chelating agents, adjuvants, dispersants, humectants, preservatives, binders, colorants, or combinations thereof.

The topical composition may be provided in a topical format, which may include a carrier for topical administration. In various embodiments, the topical composition may be provided as a contained dry powder for administration as a powder or for mixing with a base component comprising a vehicle or carrier to produce a colloid or emulsion (o/w, w/o), cream, lotion, ointment, foam, aqueous or non-aqueous gel, aqueous or non-aqueous solution, which may include a dispersion, nail lacquer, bath, or paste. When administered as a powder, the topical composition including statin may include powder base components.

The topical composition may include a base component including a carrier comprising one or more carriers or carrier components thereof. The carrier may be liquid, semi-liquid, or solid. For example, the carrier may include an aqueous, organic, or inorganic solution, which may include a dispersion or suspension, cream, gel, ointment, lotion, emulsion, powder, or paste. In some embodiments, the carrier includes a carrier or vehicle composition such as a base cream, ointment, gel, lotion, foam, or solution. The carrier may include carrier components such as lecithin, phospholipids, glycols, paraffin, fatty acids, carbopols/carbomers, alcohols, lanolin, for example.

In some embodiments, the carrier comprises an aqueous solution. In some examples, the carriers comprising aqueous solutions may be combined with the one or more active agents to formulate the topical composition as an irrigation solution, a footbath, a nail lacquer, a topical spray or soak, for example. In an embodiment, the carrier or component thereof may include an aqueous solution comprising a saline solution. For example, the topical composition may comprise a carrier or component comprising a sodium hydroxide solution, which may be a sterile solution, an alcohol, water, e.g., purified water, water for irrigation, water for injection, or a sterile water. In one embodiment, a carrier or component comprises a sodium chloride 0.09% solution (sterile). The carrier or component may be present in an amount sufficient to obtain the desired amount of active agents per unit weight or volume.

The topical composition may include a carrier comprising a polyethylene glycol (PEG) carrier component. In other embodiments, the composition is PEG-free. In these or other embodiments, the composition may include a silicon or silicon variant carrier component. In some embodiments, the composition is silicon-free. An example topical composition may comprise a solution including carrier components selected from water, alcohol, DMSO, saline or sodium chloride, sodium hypochlorite, or other aqueous or non-aqueous carrier medium into which the one or more active agents are mixed, dispersed, solubilized, or dissolved. The topical composition may be water soluble/miscible or formulated for water absorption. The topical composition may comprise a water-in-oil emulsion or oil-in-water emulsion. In one embodiment, the topical composition comprises a emulsion, e.g., a cream or lotion format, comprising one or more carrier components selected from of an acrylate copolymer, alcohol, camphor, carbomer, dimethyl isosorbide, disodium EDTA, dl-alpha tocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof. In some embodiments, the topical composition comprises a foam format that includes propellant carrier component such as butane. Topical compositions comprising a foam format may also comprise additional characteristics such as that of an emulsion, such as an oil-in-water emulsion, or gel.

In one example, the topical composition comprises an ointment format and includes active agents in a carrier comprising carrier components selected from hydrophilic petrolatum, white petrolatum, hydrophilic ointment, white ointment, anhydrous lanolin, hydrous lanolin, PEG ointment, or combinations thereof. Thus, a contained powder including the statin component alone or together with one or more of naltrexone, an antimicrobial agent, or other additional active agent may be combined with a carrier comprising hydrophilic petrolatum, white petrolatum, hydrophilic ointment, white ointment, anhydrous lanolin, hydrous lanolin, PEG ointment, or combination thereof to formulate a topical composition comprising an ointment.

In an embodiment, the topical composition comprises a gel format. The gel may be an aqueous or non-aqueous gel. The gel may include carrier components thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof. The topical composition may include a powder format and include carrier components such as lactose or talc, for example.

The topical composition or carrier thereof may include carrier components such as one or more solubilizers, stabilizers, buffers, tonicity modifiers, bulking agents, viscosity enhancers/reducers, surfactants, chelating agents, adjuvants, or combinations thereof.

In various embodiments, the topical composition or carrier thereof comprises one or more glucose polymers such as a starch, cellulose, polydextrose, or combination thereof. Example starches may include sodium starch glycolate, corn starch, pregelatinized starch, or combination thereof. Example celluloses may include hydroxypropyl cellulose, hypromellose, croscarmellose sodium, ethyl cellulose, microcrystalline cellulose, or combination thereof. Povidone such as povidone K30, copovidone, crospovidone, or combination thereof, may also be present. In some embodiments, glycol and/or a sugar alcohol may be present. Example glycols may include polyethylene glycol, propylene glycol, or combination thereof. Example sugar alcohols may include mannitol. Some embodiments may include oxides such as silicon dioxide, titanium dioxide, ferric oxide, or combination thereof. One embodiment may include any of the above and magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof. In one embodiment, the topical composition does not include one or more of starch, cellulose, polydextrose, sodium starch glycolate, corn starch, pregelatinized starch, hydroxypropyl cellulose, hypromellose, croscarmellose sodium, ethyl cellulose, microcrystalline cellulose, povidone, povidone K30, copovidone, crospovidone, polyethylene glycol, propylene glycol, mannitol, silicon dioxide, titanium dioxide, ferric oxide, magnesium stearate, talc, diethyl phthalate, sodium stearyl fumarate, sodium lauryl sulfate, polysorbate, triacetin, polacrilin, lactose, glycerol behenate, polyvinyl alcohol, carnauba wax, or combination thereof.

In some embodiments, the carrier comprises a water washable, moisturizing ointment comprising polyethylene glycol, meadowsweet extract, zinc acetate, and propylene glycol. In one embodiment, the polyethylene glycol comprises PEG-8 and PEG-75. Thus, a contained powder including the statin component alone or together with one or more of naltrexone, an antimicrobial agent, or other additional active agent may be combined with a carrier comprising a water washable, moisturizing ointment comprising polyethylene glycol, meadowsweet extract, zinc acetate, and propylene glycol. In one embodiment, the polyethylene glycol comprises PEG-8 and PEG-75.

Diluents may include aqueous or non-aqueous diluents such as water, saline solution, or sodium hypochlorite, or powders such as lactose, talc, dusting powder, starch, aluminum silicate, hydrous magnesium silicate, zinc oxide, or combinations thereof, for example. Solubilizers may include alcohols, water, DMSO, or other suitable agents, for example. Viscosity modifiers may include carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof, for example. Humectants may include glycerin, lecithin, propylene glycol, or combinations thereof, for example. Chelating agents may include EDTA or others, for example. Dispersants may include xylitol, poloxamers, or combinations thereof, for example.

In various embodiments, the topical composition comprising statin comprises a base component including xylitol, poloxamers, or both, which may be included in a compounded capsule, premix, or separate of statin powder. For example, xylitol, poloxamers, or both may comprise a powder mixed with the statin powder in a pharmaceutical container or may be in a separate pharmaceutical container, such as a capsule, satchel, powder pack, or other suitable container for containing pharmaceutical dry powders, that may be further compounded with base component in a compounded premix or administration composition. In one embodiment, the topical composition comprising statin includes LoxaSperse™ distributed by PCCA, 9901 South Wilcrest Drive, Houston, TX 77099, which includes a blend of micronized xylitol and poloxamers.

In one example, a base component comprises a powder carrier or diluent. A powder carrier or diluent may include lactose, talc, dusting powder, starch, aluminum silicate, hydrous magnesium silicate, zinc oxide, or combinations thereof, for example. Ointment carriers may include petrolatum, mineral oil, lanolin, silicones, dimethicone, or zinc oxide, for example.

In various embodiments, one or more base components may be utilized alone or in combination to formulate a topical composition comprising statin comprising a format other than a powder, e.g., solution, suspension, gel, ointment, cream, lotion, or paste.

As noted above, a base component may comprise a carrier, which may comprise a diluent. The topical treatment may include a base component including a carrier and/or may be formulated for further compounding or mixing with a base component comprising a carrier to formulate a composition comprising an administration composition.

In one aspect, the statin component comprises a contained powder alone or together with one or more of naltrexone, an antimicrobial agent, or other additional active agent, for mixing with a powder base to formulate a composition for topical administration to a wound. In a further example, the statin component comprises a contained powder alone or together with one or more of naltrexone, an antimicrobial agent, or other additional active agent, for mixing with a base component comprising an ointment carrier to formulate another composition comprising an ointment for topical administration to a wound. In still another example, the statin component comprises a contained powder alone or together with one or more of naltrexone, an antimicrobial agent, or other additional active agent, for mixing with a base component comprising a liquid carrier to formulate another composition comprising a liquid composition for topical administration to a wound in a spray, bath, or irrigation. The contained powder may comprise one or more statin oral tablets ground to a fine powder. The contained powder may comprise a fine powder of bulk statin powder. Either contained fine powder may comprise an administration composition or may be combined with a base component prior to administration as described herein. For example, a base powder, solution, or ointment may be added to a contained fine powder comprising ground tablets, wherein the added base is in addition to the oral tablet inactive ingredients. In one example, the contained powder includes xylitol, poloxamer, or both, such as LoxaSperse™.

In various embodiments, an above composition may further include an additional active component described herein or may be co-administered with another composition comprising the additional active component. For example, an above composition may be co-administered with a second composition comprising an antimicrobial, naltrexone, collagenase, or other additional active drug. In one example, the second composition comprises a powder, ointment, solution, paste, gel, lotion, or cream. In a further example, the second composition comprises a commercially available medicated composition comprising all or a portion of the additional active component. In one embodiment, the statin containing composition may be combined with the second composition prior to administration.

In some embodiments, a statin component containing composition includes or is formulated for combining with a base component comprising an ointment carrier. For example, an ointment carrier may comprise hydrophilic petrolatum, white petrolatum, hydrophilic ointment, white ointment, anhydrous lanolin, hydrous lanolin, PEG ointment, or combinations thereof. In some formulations ointment carriers may include water soluble/miscible, emulsion (o/w or w/o), absorption, or oleaginous ointment carriers. Soluble/miscible ointment carriers may include water soluble/miscible PEG ointments, for example. Emulsion carriers may include hydrophilic ointments, cold cream, vanishing cream, or hydrous lanolin, for example. Oleaginous bases may include hydrocarbons, white petrolatum, or white ointment. Absorption carriers may include anhydrous lanolin, for example.

In various embodiments, one or more base components comprise lecithin, phospholipids, glycols, paraffin, fatty acids, carbopols/carbomers, alcohols, lanolin, or combination thereof, for example. In one embodiment, a base component includes a carrier comprising a sodium chloride 0.09% solution (sterile). Some embodiments may include base components including polyethylene glycol (PEG), while other embodiments may be PEG-free. In an above embodiment or another embodiment, a base component may include a carrier including a silicon or silicon variant or may be silicon-free. A base component comprising a carrier solution may comprise aqueous or non-aqueous liquids. Example solutions may include water, alcohol, DMSO, saline or sodium chloride, sodium hypochlorite, or hydrogen peroxide. In some embodiments, the carrier comprises an aqueous solution such as a saline solution. For example, the statin component may comprise or be formulated for combining with a base component comprising a sodium hydroxide solution carrier, which may be a sterile solution, an alcohol, water, e.g., purified water, water for irrigation, water for injection, or a sterile water. The carrier may be water soluble/miscible or formulated for water absorption, such as a gel.

In some embodiments, a statin component containing composition of the disclosed topical treatment includes or is formulated for combining with a base component comprising a water-in-oil emulsion or oil-in-water emulsion carrier. For example, the carrier may comprise an emulsion having a cream or lotion format including one or more of acrylate copolymers, alcohol, camphor, carbomer, dimethyl isosorbide, disodium EDTA, dl-alpha tocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate (e.g., polysorbate 85, polysorbate 20), purified water, titanium dioxide, tridecyl stearate, tridecyl trimellitate, sodium hydroxide, sodium hydroxide, sorbitol, stearic acid, zinc pyrithione, or combinations thereof.

In some embodiments, a statin component containing composition of the herein described topical treatment includes or is formulated for combining with a base component comprising a gel carrier. Example gel carriers may be an aqueous or non-aqueous gel. The gel may include thickening agents and/or gelling agents such as carbopol, poloxamer, xanthan gum, methylcellulose, carboxymethyl cellulose, hydroxyethyl cellulose, ethylcellulose, gelatin, magnesium aluminum silicate, polyvinyl alcohol, sodium alginate, or combinations thereof.

Further to the above, in some embodiments, a base component includes a commercially available base carrier for compounding. The base carrier may be liquid, semi-liquid, or solid. For example, the base carrier may include an aqueous, organic, or inorganic solution, which may include a dispersion or suspension, cream, gel, ointment, lotion, emulsion, powder, or paste. Thus, a method of formulating a composition according to the herein described topical treatment may include addition of one or more statins, e.g., pharmaceutical bulk powders and/or ground tablets, to a topical base carrier for compounding to formulate creams, ointments, solutions/irrigations/baths, powders, gels, lotions, or pastes, for example. Non-limiting examples may include Spira-Wash® Gel, Lipoderm®, Loxasperse®, Mucolox™, or Versabase® Cream, Goam, Gel, Lotion or Shampoo, manufactured and distributed by PCCA, 9901 South Wilcrest Drive, Houston, TX 77099.

As introduced above and described further below, a statin component containing composition of the herein described topical treatment may include an active component comprising one or more statins and a base component formulated as a premix for further mixing with additional base component, which may be or include a carrier vehicle and may comprise a diluent, to formulate a composition for administration or may itself comprise a composition for administration. Thus, the statin component containing composition may comprise an administration dosage form comprising one or more statins and one or more base components for topical administration to a wound in a powder, ointment, or liquid format.

In some embodiments, the compound composition comprises topical composition premix including one or more statins and a base component having a powder, ointment, or liquid format for further mixing with one or more additional base components such as a carrier, which may include a diluent, powder, liquid, or ointment. For example, a second base component comprising carrier and/or diluent may be further combined with the premix to formulate a composition for topical administration. In other examples, the composition comprises one or more statins compounded with a base component formulated for administration to a wound, necrotic tissue, broken tissue, unbroken tissue, or other targeted areas of the body, that may or may not be infected without additional compounding, e.g., without mixing with additional base component. As described above and elsewhere herein, the topical treatment may include an active component comprising one or more additional active drugs and/or one or more base components that may be included in a contained or otherwise contained powder including one or more statins, which in some examples may comprise a premix. In some embodiments, one or more of the powders may be provided separately for further compounding or direct administration. In various embodiments, the powders may be contained and/or otherwise contained, e.g., a vial, packet, or pouch. The statin powder may comprise bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In one embodiment, the topical treatment may comprise a powder format including one or more statins, which in some embodiments, may include a powder carrier base component, for mixing with a base component comprising a liquid carrier, which may comprise a diluent, to formulate an administration composition comprising a liquid, which may include a solution, dispersion, or suspension, for topical administration to a wound, necrotic tissue, broken tissue, unbroken tissue, or other targeted areas of the body, that may or may not be infected, in a spray, bath, or irrigation. In one embodiment, the powder comprises a compounded administration formulation for administration to the tissue without further mixing with the liquid carrier base component. As described above and elsewhere herein additional active drugs and/or base components may be included in a contained or contained powder, premix, or may be combined therewith to formulate the composition for administration. The powder may be contained or otherwise contained, e.g., a vial, packet, or pouch. Statin powder may be obtained from bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In another embodiment, the topical treatment may comprise a topical composition having a powder format including one or more statins, one or more antimicrobial agents, naltrexone, or combination thereof, which in some embodiments may include one or more base component powders, for mixing with a base component comprising a powder carrier, which may comprise a diluent, to formulate an administration formulation comprising a powder format for topical administration to a wound, necrotic tissue, broken tissue, unbroken tissue, or other targeted areas of the body, that may or may not be infected. In one embodiment, the powder format comprises a compounded administration formulation for administration to the target tissue without further mixing. As described above and elsewhere herein, when included, additional active drugs and/or base components may be included in a contained or contained powder, premix, or may be combined therewith to formulate the composition for administration. The powder may be contained or otherwise contained, e.g., a vial, packet, or pouch. Statin powder may be obtained from bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In another embodiment, the topical treatment may comprise a topical composition having a powder format including one or more statins, which in some embodiments may include one or more base component powders, for mixing with a base component comprising an ointment carrier, which may comprise a diluent, to formulate an administration formulation comprising an ointment format for topical administration to a wound, necrotic tissue, broken tissue, unbroken tissue, or other targeted areas of the body, that may or may not be infected. In one embodiment, the powder format comprises a compounded administration formulation for administration to the target tissue without further mixing. As described above and elsewhere herein additional active drugs and/or base components may be included in a contained or contained powder, premix, or may be combined therewith to formulate the composition for administration. The powder may be contained or otherwise contained, e.g., a vial, packet, or pouch. Statin powder may be obtained from bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In another embodiment, the topical treatment comprises a topical composition having an ointment format, which may include an ointment base component, for mixing with a base component comprising liquid carrier, which may comprise a diluent, to formulate an administration formulation comprising a liquid or emulsion for topical administration to a wound, necrotic tissue, broken tissue, unbroken tissue, or other targeted areas of the body, that may or may not be infected in a spray, bath, or irrigation. In one embodiment, the ointment format comprises a compounded administration formulation for administration to the target tissue without further mixing. As described above and elsewhere herein, when included, additional active drugs and/or base components may be included in the ointment premix or may be combined therewith to formulate the composition for administration. The ointment may be formulated by combining statin powder with an ointment base component wherein the statin powder is obtained from bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In another embodiment, the topical treatment comprises a topical composition having a liquid format, which may include a liquid base component, for mixing with a base component comprising a powder or ointment carrier, which may comprise a diluent, to formulate an administration formulation comprising a solution, suspension, or emulsion for topical administration to a wound, necrotic tissue, broken tissue, unbroken tissue, or other targeted areas of the body, that may or may not be infected in a spray, bath, or irrigation. In one embodiment, the liquid format comprises a compounded administration formulation for administration to the target tissue without further mixing. As described above and elsewhere herein, when included, additional active drugs and/or base components may be included in the liquid premix or may be combined therewith to formulate the composition for administration. The liquid may be formulated by combining statin powder with an ointment base component wherein the statin powder is obtained from bulk powder and/or ground oral tablets. Additional active drugs may similarly comprise bulk powder and/or ground oral tablets. For example, an antimicrobial agent may comprise one or more antimicrobial drugs comprising bulk powder and/or ground oral tablets comprising an antimicrobial drug. Additionally or alternatively, the additional active component may comprise collagenase power, cream, ointment, or other format. All or a portion of the additional active component may be co-administered in a separate composition as described herein or, in some embodiments, may be combined with the statin component to formulate an administration composition.

In some examples, the statin component may be provided in a pharmaceutical container comprising one or more capsules that may be opened, broken down, or dissolved and combined with a base component, which may include multiple base components, to formulate a composition prior to administration. When included, the one or more capsules may include all or a portion of the additional active component comprising one or more additional active drugs or one or more additional active drugs may be combined with the base component separate of the satin powder to formulate a second topical composition, which, in some embodiments, may include a commercially available medicated topical composition including all or a portion of the additional active component. The one or more capsules may include one or more other base components in powder format for addition to the base component. The one or more capsules may comprise a dosage strength of the statin component for compounding with the base component to formulate a suitable dosage volume of the statin component comprising the desired dosage strength. Thus, in some embodiments, the statin component may be provided in a concentrated format comprising a powder. The powder may be contained or contained in single or multi-dose amounts. For example, contents of a capsule may be added to one or more base components to formulate a single or multi-dose composition. In one embodiment, a base component may comprise a medicated composition comprising all or a portion of the additional active component and may be combined in an amount to provide a dosage strength of the additional active component. In various embodiments, the additional active component may include additional active drugs selected from antimicrobials, NSAIDs, steroids, local anesthetics, steroids, antihistamines, collagenase, or combinations thereof. In some embodiments, other categories of active drugs may be used. One or more additional active drugs may be present in powder contained with or separate from the one or more statins. In some embodiments, one or more additional active drugs of the additional active component may comprise a solution, emulsion, cream, ointment, gel, or lotion format for addition to the one or more statin powders and/or base component.

In one embodiment, the topical treatment comprises a first topical composition comprising the statin component and a separate second topical composition comprising the additional active component for co-administered.

In some embodiments, the statin component is provided in a concentrated premix format comprising all or a portion of the active component including the one or more statins in a powder, emulsion, ointment, or liquid base component for further mixing with one or more additional base components to formulate a topical composition for administration. The concentrated premix may be provided in single or multi-dose volumes. In some embodiments, the premix may also include all or a portion of the additional active component including one or more additional active drugs selected from antimicrobials, collagenase, NSAIDs, steroids, local anesthetics, steroids, antihistamines, or combinations thereof. One or more of the additional active drugs may be provided in a powder contained with or separate from the one or more statins. In some embodiments, one or more additional active drugs may be provided in a solution, emulsion, cream, ointment, gel, paste, powder, or lotion format for addition to the one or more statin powders and/or base component. The premix may be formulated for further mixing with additional base component to formulate a powder, gel, ointment, or liquid format for topical administration.

In some embodiments, the topical treatment includes a composition comprising the statin component and a base component, which may include multiple base components, in a powder, gel, ointment, or liquid format for topical administration. The composition may be provided in single or multi-dose volume. In some embodiments, the topical composition comprising statin may include all or a portion of the additional active component, when included, comprising one or more additional active drugs selected from antimicrobials, collagenase, NSAIDs, steroids, local anesthetics, steroids, antihistamines, or combinations thereof.

As noted above, some embodiments include a first composition comprising all or a portion of the statin component and a separate second composition including all or a portion of the additional active component for co-administration. However, it will be appreciated that either the first and/or the second composition may further include a portion of the statin or additional active component. More than two compositions for co-administration may also be used. Some example first compositions may be devoid of additional active component or may include a portion of the additional active component for administration in addition to the second composition. The first composition may be administered coincident with the second composition, preferably within 10 minutes, 30 minutes, 1 hour, 4 hours, 8 hours, 12 hours, or at least within 24 hours. In some examples, the co-administration takes place prior to drying or absorbance of the co-administered composition at the body surface. The statin component may include one or more statins. In various embodiments, the statin component comprises one or more statins selected from atorvastatin, fluvastatin, lovastatin, pitavastatin, pravastatin, rosuvastatin, simvastatin, or combinations thereof. Some embodiments may include or be formulated from bulk pharmaceutical grade statin powder.

In one embodiment, the topical treatment comprises or is formulated from statin powder, ground oral statin tablets, or both.

Atorvastatin is a synthetic lipid-lowering agent. Atorvastatin is an inhibitor of 3-hydroxy-3-methylglutaryl-coenzyme A (HMG-CoA) reductase. This enzyme catalyzes the conversion of HMG-CoA to mevalonate, an early and rate-limiting step in cholesterol biosynthesis.

In various embodiments, the statin component comprises atorvastatin. Atorvastatin is available in bulk pharmaceutical grade powder. Some embodiments may alternatively or additionally include commercially available atorvastatin oral tablets ground to a fine powder. For example, the topical treatment may comprise a composition including ground atorvastatin oral tablets alone or combined with a base comprising a powder, solution, cream, lotion, ointment, gel, or paste. When the topical treatment includes an additional active component, all or a portion of the additional active component may be mixed with the atorvastatin. An additional or second composition containing all or a remaining portion of the additional active component may be co-administered with the composition containing atorvastatin. Atorvastatin oral tablets are available in 10 mg, 20 mg, 40 mg, and 80 mg tablets. Other strength tablets may be used as they become available. Example inactive ingredients may include calcium carbonate, croscarmellose sodium, hydroxypropyl cellulose, lactose monohydrate, magnesium stearate, microcrystalline cellulose, Opadry White YS-1-7040 (hypromellose, polyethylene glycol, talc, titanium dioxide), polysorbate 80, or variants thereof. In some tablets, inactive ingredients may include basic butylated methacrylate copolymer, crospovidone, hydroxypropyl cellulose, lactose monohydrate, magnesium stearate, methanol, microcrystalline cellulose, sodium bicarbonate, sodium lauryl sulfate, lecithin, polyvinyl alcohol, talc, titanium dioxide, xanthan gum, or variants thereof.

The statin component may include atorvastatin at a dosage strength between about 5 mg and about 200 mg. Thus, an administration volume of a dose of the statin component may comprise between about 5 mg and about 200 mg, such as between about 10 mg and about 80 mg, about 20 mg and about 60 mg, about 80 mg and about 200 mg, about 100 mg and about 200 mg, about 150 mg and about 200 mg atorvastatin. In embodiments including multiple statins, the total amount of statin present in a dose may typically be between about 5 mg and about 200 mg. Thus, in embodiments including atorvastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 10 mg and about 80 mg, atorvastatin. Additionally, a topical treatment comprising a powder, ointment, emulsion, or liquid premix composition including one or more base components for further combining with one or more additional base components may comprise between about 5 mg and about 200 mg atorvastatin in a single dose volume. Some embodiments may include atorvastatin dosage amounts between about 5 mg and 70 mg, about 20 mg and about 50 mg, about 10 mg and about 30 mg, about 30 mg and about 1800 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of atorvastatin between about 5 mg and about 200 mg may include atorvastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes atorvastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. As noted above, some embodiments may include multiple dosages from which multiple dosages may be formulated and/or administered.

In various embodiments, the statin component comprises fluvastatin. Fluvastatin is a cholesterol lowering agent that inhibits 3-hydroxy-3-methylglutaryl coenzyme A (HMG-CoA) reductase. Fluvastatin is available in bulk pharmaceutical grade powder. Some embodiments may alternatively or additionally include commercially available fluvastatin oral capsules or tablets ground to a fine powder. For example, the topical treatment may comprise a composition including ground fluvastatin oral tablets alone or combined with a base comprising a powder, solution, cream, lotion, ointment, gel, or paste. When the topical treatment includes an additional active component, all or a portion of the additional active component may be mixed with the fluvastatin. An additional or second composition containing all or a remaining portion of the additional active component may be co-administered with the composition containing fluvastatin. Fluvastatin oral tablets are available in 80 mg extended release tablets, capsules are available in 20 mg and 40 mg. Other strengths may be used as they become available. Fluvastatin 80 mg tablets may include extended release tablets that may include inactive ingredients such as microcrystalline cellulose, hydroxypropyl methylcellulose, potassium bicarbonate, povidone, colloidal silicon dioxide, corn starch, hydroxypropyl cellulose, hypromellose, lecithin, magnesium stearate, polyethylene glycol, polyvinyl alcohol, iron oxide, sodium lauryl sulfate, talc, titanium dioxide, or variants thereof.

The statin component may include fluvastatin at a dosage strength between about 5 mg and about 200 mg, e.g., between about 20 mg and about 80 mg. Thus, an administration volume of a dose of the statin component may comprise about 5 mg and about 200 mg, such as between about 10 mg and about 80 mg, about 20 mg and about 60 mg, about 80 mg and about 200 mg, about 100 mg and about 200 mg, about 150 mg and about 200 mg fluvastatin. In embodiments including multiple statins, the total amount of statin present in a dose may typically be between about 5 mg and about 200 mg. Thus, in embodiments including fluvastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 20 mg and about 80 mg fluvastatin. Additionally, a topical treatment comprising a powder, ointment, emulsion, or liquid premix composition including one or more base components for further combining with one or more additional base components may comprise between about 20 mg and about 80 mg fluvastatin in a single dose volume. Some embodiments may include fluvastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of fluvastatin between about 5 mg and about 200 mg may include fluvastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes fluvastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. As noted above, some embodiments may include multiple dosages from which multiple doses may be formulated and/or administered.

In various embodiments, the statin component comprises lovastatin. Lovastatin is a cholesterol lowering agent isolated from a strain of *Aspergillus terreus*. After oral ingestion, lovastatin, which is an inactive lactone, is hydrolyzed to the corresponding β-hydroxyacid form. This is a principal metabolite and an inhibitor of 3-hydroxy-3-methylglutaryl-coenzyme A (HMG-CoA) reductase. This enzyme catalyzes the conversion of HMG-CoA to mevalonate, which is an early and rate limiting step in the biosynthesis of cholesterol.

Lovastatin is available in bulk pharmaceutical grade powder. Some embodiments may alternatively or additionally include commercially available lovastatin oral tablets ground to a fine powder. For example, the topical treatment may comprise a composition including ground lovastatin oral tablets alone or combined with a base comprising a powder, solution, cream, lotion, ointment, gel, or paste. When the topical treatment includes an additional active component, all or a portion of the additional active component may be mixed with the lovastatin. An additional or second composition containing all or a remaining portion of the additional active component may be co-administered with the composition containing lovastatin. Lovastatin oral tablets are available in 10 mg, 20 mg, and 40 mg tablets. Other strength tablets may be used as they become available. Example inactive ingredients may include lactose anhydrous, lactose monohydrate, magnesium stearate, microcrystalline cellulose, poloxamer, pregelatinized starch, sodium starch glycolate, butylated hydroxyanisole, talc, or variants thereof. Tablets may also contain pigment blend light orange, FD&C Blue #2 Aluminum Lake, Lake blend green, FD&C Yellow #6 Aluminum Lake, FD&C Blue #1 Aluminum Lake, D&C Yellow #10 Aluminum Lake. The statin component may include lovastatin at a dosage strength about 5 mg and about 200 mg. Thus, an administration volume of a dose of the statin component may comprise between about 5 mg and about 200 mg, such as between about 10 mg and about 80 mg, about 20 mg and about 60 mg, about 80 mg and about 200 mg, about 100 mg and about 200 mg, about 150 mg and about 200 mg lovastatin. In embodiments including multiple statins, the total amount of statin present in a dose may typically be between about 5 mg and about 200 mg. Thus, in embodiments including lovastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 10 mg and about 60 mg lovastatin. Additionally, a topical treatment composition comprising a powder, ointment, emulsion, or liquid premix composition including one or more base components for further combining with one or more additional base components may comprise between about 5 mg and about 200 mg, e.g., between about 10 mg and about 60 mg lovastatin in a single dose volume.

Some embodiments may include lovastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of lovastatin between about 5 mg and about 200 mg may include lovastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes lovastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. As noted above, some embodiments may include multiple dosages from which multiple dosages may be formulated and/or administered.

In various embodiments, the statin component comprises pitavastatin. Pitavastatin is a synthetic lipid-lowering agent. Pitavastatin is an inhibitor of 3-hydroxy-3-methylglutaryl-coenzyme A (HMG-CoA) reductase. Pitavastatin is available in bulk pharmaceutical grade powder. Some embodiments may alternatively or additionally include commercially available pitavastatin calcium or pitavastatin magnesium oral tablets ground to a fine powder. For example, the topical treatment may comprise a composition including ground pitavastatin oral tablets alone or combined with a base comprising a powder, solution, cream, lotion, ointment, gel, or paste. When the topical treatment includes an additional active component, all or a portion of the additional active component may be mixed with the pitavastatin. An additional or second composition containing all or a remaining portion of the additional active component may be co-administered with the composition containing pitavastatin. Pitavastatin calcium and pitavastatin magnesium oral tablets are available in 1 mg, 2 mg, and 4 mg strength pitavastatin tablets. Other strength tablets may be used as they become available. Example inactive ingredients contained in pitavastatin calcium tablets include calcium carbonate, hypromellose, lactose monohydrate, crospovidone, low substituted hydroxypropylcellulose, hypromellose, magnesium aluminometasilicate, magnesium stearate, sodium carbonate anhydrous, or variants thereof, and a film coating containing hypromellose, titanium dioxide, polyethylene glycol, talc, triethyl citrate, colloidal anhydrous silica, or variants thereof.

The statin component may include pitavastatin at a dosage strength between about 5 mg and about 200 mg. Thus, an administration volume of a dose of the statin component may comprise between about 5 mg and about 200 mg, such as between about 10 mg and about 80 mg, about 20 mg and about 60 mg, about 80 mg and about 200 mg, about 100 mg and about 200 mg, about 150 mg and about 200 mg pitavastatin. In embodiments including multiple statins, the total amount of statin present in a dose may typically be between about 5 mg and about 200 mg. Thus, in embodiments including pitavastatin and another statin, the total amount of statin present in the topical composition may be between about 5 mg and about 200 mg, including any range of total statin therebetween or combination of ranges therebetween with respect to the represented statins. In some embodiments, the statin component may include pitavastatin in an administration dosage strength between about 1 mg and about 4 mg. Similarly, a topical treatment comprising contained statin component powder for mixing with one or more base components to formulate a premix or administration composition comprising a single dose may comprise between about 5 mg and about 200 mg. In another embodiment, a single dose may comprise between about 1 mg and about 4 mg pitavastatin. Additionally, a topical treatment comprising a powder, ointment, emulsion, or liquid premix composition including one or more base components for further combining with one or more additional base components may comprise between about 5 mg and about 200 mg pitavastatin or between about 1 mg and about 4 mg pitavastatin in a single dose volume. Some embodiments may include pitavastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of pitavastatin between about 5 mg and about 200 mg may include pitavastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes pitavastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. Some embodiments may include pitavastatin dosage amounts between about 1.5 mg and 4 mg, about 1.5 mg and about 3.5 mg, about 1.5 mg and about 3 mg, about 1.5 mg and about 2.5 mg, about 1.5 mg and about 2 mg, about 2 mg and about 4 mg, about 2 mg and about 3.5 mg, about 2 mg and about 3 mg, about 2 mg and about 2.5 mg, about 3 mg and about 4 mg, about 3 mg and about 3.5 mg, about 4.5 mg and about 4 mg, such as greater than about 1 mg, about 1.5 mg, about 2 mg, about 2.5 mg, about 3 mg, about 3.5 mg, or about 4 mg. In various embodiments, the statin component includes pitavastatin dosage amounts of about 1 mg, about 1.5 mg, about 2 mg, about 2.5 mg, about 3 mg, about 3.5 mg, or about 4 mg. As noted above, some embodiments may include multiple dosages from which multiple dosages may be formulated and/or administered.

In various embodiments, the statin component comprises pravastatin. Pravastatin is one of a class of lipid-lowering compounds, the statins, which reduce cholesterol biosynthesis. These agents are competitive inhibitors of HMG-CoA reductase, the enzyme catalyzing the early rate-limiting step in cholesterol biosynthesis, conversion of HMG-CoA to mevalonate.

Pravastatin is available in bulk pharmaceutical grade powder. Some embodiments may alternatively or additionally include commercially available pravastatin sodium oral tablets ground to a fine powder. For example, the topical treatment may comprise a composition including ground pravastatin oral tablets alone or combined with a base comprising a powder, solution, cream, lotion, ointment, gel, or paste. When the topical treatment includes an additional active component, all or a portion of the additional active component may be mixed with the pravastatin. An additional or second composition containing all or a remaining portion of the additional active component may be co-administered with the composition containing pravastatin. Pravastatin sodium oral tablets are available in 10 mg, 20 mg, 40 mg, and 80 mg strength pravastatin tablets. Other strength tablets may be used as they become available. Example inactive ingredients may include croscarmellose sodium, lactose monohydrate, crospovidone, magnesium oxide, sodium stearyl fumarate, magnesium stearate, microcrystalline cellulose, povidone, polyoxyl 35 castor oil, or variants thereof. Additional inactive ingredients may include ferric oxide red, ferric oxide yellow, D&C yellow No. 10 aluminum lake, FD&C blue No. 1 aluminum lake, Opadry white YS-1-7040, or others.

The statin component may include pravastatin at a dosage strength between about 5 mg and about 200 mg. Thus, an administration volume of a dose of the statin component may comprise between about 5 mg and about 200 mg, such as between about 10 mg and about 80 mg, about 20 mg and about 60 mg, about 80 mg and about 200 mg, about 100 mg and about 200 mg, about 150 mg and about 200 mg pravastatin. In embodiments including multiple statins, the total amount of statin present in a dose may typically be between about 5 mg and about 200 mg. Thus, in embodiments including pravastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 10 mg and about 80 mg pravastatin. Additionally, a topical treatment comprising a powder, ointment, emulsion, or liquid premix composition including one or more base components for further combining with one or more additional base components may comprise between about 5 mg and about 200 mg, e.g., between about 10 mg and about 80 mg pravastatin in a single dose volume.

Some embodiments may include pravastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of pravastatin between about 5 mg and about 200 mg may include pravastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes pravastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. As noted above, some embodiments may include multiple dosages from which multiple dosages may be formulated and/or administered.

In various embodiments, the statin component comprises rosuvastatin. Rosuvastatin is one of a class of lipid-lowering compounds, the statins, which reduce cholesterol biosynthesis. These agents are competitive inhibitors of HMG-CoA reductase, the enzyme catalyzing the early rate-limiting step in cholesterol biosynthesis, conversion of HMG-CoA to mevalonate.

Rosuvastatin is available in bulk pharmaceutical grade powder. Some embodiments may alternatively or additionally include commercially available rosuvastatin sodium oral tablets ground to a fine powder. For example, the topical treatment may comprise a composition including ground rosuvastatin oral tablets alone or combined with a base comprising a powder, solution, cream, lotion, ointment, gel, or paste. When the topical treatment includes an additional active component, all or a portion of the additional active component may be mixed with the rosuvastatin. An additional or second composition containing all or a remaining portion of the additional active component may be co-administered with the composition containing rosuvastatin. Rosuvastatin sodium oral tablets are available in 5 mg, 10 mg, 20 mg, and 40 mg strength rosuvastatin tablets. Other strength tablets may be used as they become available. Example inactive ingredients may include microcrystalline cellulose, lactose monohydrate, tribasic calcium phosphate, polydextrose, polyethylene glycol, crospovidone, magnesium stearate, hypromellose, triacetin, titanium dioxide, or variants thereof. Additional inactive ingredients may include ferric oxide red, ferric oxide yellow, FD&C yellow No. 5 tartrazine aluminum lake, FD&C yellow No. 6 sunset yellow FCF aluminum lake, FD&C Blue No. 2 Aluminum Lake, FD&C Yellow No. 6 Aluminum Lake, or others.

The statin component may include rosuvastatin at a dosage strength between about 5 mg and about 200 mg. Thus, an administration volume of a dose of the statin component may comprise between about 5 mg and about 200 mg, such as between about 10 mg and about 40 mg, about 20 mg and about 60 mg, about 80 mg and about 200 mg, about 100 mg and about 200 mg, about 150 mg and about 200 mg rosuvastatin. In embodiments including multiple statins, the total amount of statin present in a dose may typically be between about 5 mg and about 200 mg. Thus, in embodiments including rosuvastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 5 mg and about 40 mg rosuvastatin. Additionally, a topical composition comprising statin comprising a powder, ointment, emulsion, or liquid premix composition including one or more base components for further combining with one or more additional base components may comprise between about 5 mg and about 200 mg, e.g., between about 5 mg and about 40 mg rosuvastatin in a single dose volume. Some embodiments may include rosuvastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of rosuvastatin between about 5 mg and about 200 mg may include rosuvastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes rosuvastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. Some embodiments may include rosuvastatin dosage amounts between about 5 mg and about 35 mg, about 5 mg and about 30 mg, about 5 mg and about 25 mg, about 5 mg and about 20 mg, about 5 mg and about 15 mg, about 5 mg and about 10 mg, about 10 mg and about 40 mg, about 10 mg and about 30 mg, about 10 mg and about 25 mg, about 10 mg and about 20 mg, about 20 mg and about 40 mg, about 20 mg and about 35 mg, about 20 mg and about 30 mg, about 20 mg and about 25 mg, about 30 mg and about 40 mg, about 30 mg and about 35 mg, about 35 mg and about 40 mg, such as greater than about 5 mg, about 10 mg, about 15 mg, about 25 mg, about 30 mg, or about 35 mg. In various embodiments, the statin component includes rosuvastatin dosage amounts of about 5 mg, about 10 mg, about 15 mg, about 25 mg, about 30 mg, or about 35 mg. As noted above, some embodiments may include multiple dosages from which multiple dosages may be formulated and/or administered.

In various embodiments, the statin component comprises simvastatin. Simvastatin is a lipid-lowering agent that is derived synthetically from a fermentation product of *Aspergillus terreus*. After oral ingestion, simvastatin, which is an inactive lactone, is hydrolyzed to the corresponding β-hydroxyacid form. This is an inhibitor of 3-hydroxy-3-methylglutaryl-coenzyme A (HMG-CoA) reductase. This enzyme catalyzes the conversion of HMG-CoA to mevalonate, which is an early and rate-limiting step in the biosynthesis of cholesterol.

Simvastatin is available in bulk pharmaceutical grade powder. Some embodiments may alternatively or additionally include commercially available simvastatin tablets for oral administration. For example, the topical treatment may comprise a composition including ground simvastatin oral tablets alone or combined with a base comprising a powder, solution, cream, lotion, ointment, gel, or paste. When the topical treatment includes an additional active component, all or a portion of the additional active component may be mixed with the simvastatin. An additional or second composition containing all or a remaining portion of the additional active component may be co-administered with the composition containing simvastatin. Simvastatin tablets are available in 5 mg, 10 mg, 20 mg, 40 mg or 80 mg strengths. Other strengths may be used as they come available. Example inactive ingredients include microcrystalline cellulose, hydroxypropyl cellulose, hypromellose E5, croscarmellose sodium, ferric oxide red, lactose monohydrate, magnesium stearate, maize starch, talc, titanium dioxide, butylated hydroxyanisole, ascorbic acid, citric acid monohydrate, triethyl citrate, and variants thereof. Additional inactive ingredients may include ferric oxide red, ferric oxide yellow, or others.

The statin component may include simvastatin at a dosage strength between about 5 mg and about 200 mg. Thus, an administration volume of a dose of the statin component may comprise between about 5 mg and about 200 mg, such as between about 10 mg and about 80 mg, about 20 mg and about 60 mg, about 80 mg and about 200 mg, about 100 mg and about 200 mg, about 150 mg and about 200 mg simvastatin. In embodiments including multiple statins, the total amount of statin present in a dose may typically be between about 5 mg and about 200 mg. Thus, in embodiments including simvastatin and another statin, the total amount of statin present in the topical composition may be between about 5 mg and about 200 mg, including any range of total statin therebetween or combination of ranges therebetween with respect to the represented statins. Similarly, a topical treatment comprising contained statin component powder for mixing with one or more base components to formulate a premix or administration composition comprising a single dose may comprise between about 5 mg and about 200 mg, e.g., between about 5 mg and about 80 mg simvastatin. Additionally, a topical treatment comprising a powder, ointment, emulsion, or liquid premix composition including one or more base components for further combining with one or more additional base components may comprise between about 5 mg and about 200 mg, e.g., between about 5 mg and about 80 mg simvastatin in a single dose volume. Some embodiments may include simvastatin dosage amounts between about 5 mg and 70 mg, about 20 mg and about 50 mg, about 10 mg and about 30 mg, about 30 mg and about 180 mg, about 30 mg and about 80 mg, about 40 mg and about 180 mg, about 50 mg and about 180 mg, about 80 mg and about 180 mg, about 90 mg and about 180 mg, about 30 mg and about 60 mg, about 40 mg and about 80 mg, about 60 mg and about 100 mg, about 100 mg and about 150 mg, about 150 mg and about 200 mg, about 60 mg and about 100 mg, or about 70 mg and about 150 mg. For example, dosage amounts of simvastatin between about 5 mg and about 200 mg may include simvastatin in an amount greater than about 10 mg, greater than about 20 mg, greater than about 40 mg, greater than about 60 mg, greater than about 80 mg, greater than about 100 mg, greater than about 120 mg, greater than about 140 mg, greater than about 160 mg, or greater than about 180 mg. In various embodiments, the statin component includes simvastatin dosage amounts of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 170 mg, about 180 mg, or about 200 mg. As noted above, some embodiments may include multiple dosages from which multiple dosages may be formulated and/or administered.

As introduced above, in some embodiments, the topical treatment includes an additional active component within the same and/or an additional topical composition.

The topical treatment may be contained within or the statin component may be provided in one or more pharmaceutical containers, such as a capsule, satchel, powder pack, or other suitable container for containing pharmaceutical dry powders, that may be opened, broken down, or dissolved and combined with a base component, which may include multiple base components, to formulate a composition prior to administration. When included, the one or more pharmaceutical containers may include all or a portion of the additional active component comprising one or more additional active drugs or one or more additional active drugs may be combined with the base component separate of the satin powder to formulate a second topical composition, which, in some embodiments, may include a commercially available medicated topical composition including all or a portion of the additional active component. The one or more pharmaceutical containers may include one or more other base components in powder format for addition to the base component. The one or more pharmaceutical containers may comprise a dosage strength of the statin component for compounding with the base component to formulate a suitable dosage volume of the statin component comprising the desired dosage strength. Thus, in some embodiments, the statin component may be provided in a concentrated format comprising a powder. The powder may be contained or contained in single or multi-dose amounts. For example, contents of a pharmaceutical container may be added to one or more base components to formulate a single or multi-dose composition. In one embodiment, a base component may comprise a medicated composition comprising all or a portion of the additional active component and may be combined in an amount to provide a dosage strength of the additional active component. In various embodiments, the additional active component may include additional active drugs selected from antimicrobials, NSAIDs, steroids, local anesthetics, steroids, antihistamines, collagenase, or combinations thereof. In some embodiments, other categories of active drugs may be used. One or more additional active drugs may be present in powder contained with or separate from the one or more statins. In some embodiments, one or more additional active drugs of the additional active component may comprise a solution, emulsion, cream, ointment, gel, or lotion format for addition to the one or more statin powder and/or base component.

In various embodiments, the topical treatment includes naltrexone as an additional active agent along with the statin component. Naltrexone may be present in a dosage amount between about 1 mg and about 50 mg, such as between about 1 mg and about 10 mg, about 1 mg and about 30 mg, about 10 mg and about 50 mg, about 10 mg and about 30 mg, about 20 mg and about 50 mg, about 20 mg and about 35 mg, or about 30 mg and about 50 mg. In one example, naltrexone is present in an amount greater than 5 mg, greater than 10 mg, greater than 20 mg, greater than 30 mg, or greater than 40 mg. Naltrexone may be provided from bulk powder or from crushed naltrexone tablets. In some embodiments, in addition to one or more statins and one or more additional actives including naltrexone, the topical composition includes base components comprising one or more of colloidal anhydrous silica, crospovidone, hydroxypropyl methylcellulose, lactose monohydrate, magnesium stearate, microcrystalline cellulose, polyethylene glycol 400, or polysorbate 80. In another example, the base components comprise one or more of carnauba wax powder, colloidal silicon dioxide, croscarmellose sodium, hypromellose, hydroxypropyl cellulose, lactose anhydrous, magnesium stearate, microcrystalline cellulose, polyethylene glycol. The statin component and naltrexone may be provided together or separate within a pharmaceutical container as dry powders. The dry powders may be removed from the pharmaceutical containers and administered to target tissue surfaces directly as a powder or may be further combined with a base component to formulate a solution, lotion, paste, cream, ointment, emulsion, or gel. In another example, the topical treatment comprises naltrexone powder in a separate pharmaceutical container or container for further compounding with statin powder and/or one or more base components to formulate a compounded premix or administration composition. In some embodiments, all or a portion of the naltrexone is provided in a separate second composition comprising a solution, lotion, paste, cream, ointment, emulsion, or gel for co-administration as described herein. Thus, various embodiments of the examples and embodiments of the compositions described above and elsewhere herein comprising one or more statins may further comprise naltrexone or may be provided in separate compositions for co-administration with an additional composition comprising naltrexone.

In one example, the topical treatment includes a statin component comprising one or more statins in a dosage amount described above or elsewhere herein, such as between about 5 mg and about 200 mg, with one or more antimicrobials. It is to be appreciated that larger or bulk preparations of the topical composition may be formulated from which multiple dosage volumes of the topical composition may be withdrawn for administration. In such configurations, the preparation may be provided in concentrations from which dosages of the actives and inactives are present in suitable concentrations to provide the described dosages. In some embodiments, the topical composition includes a pharmaceutical composition including one or more statins in a dosage amount described above or elsewhere herein, such as between about 5 mg and about 200 mg, in a dry-powder combined with a base component. The base component may comprise or consist of petrolatum, a water-washable-ointment, or a cream base or cream-type vehicle. In various embodiments, the topical composition comprises an additional active selected from one or more antifungals, antibacterials, antivirals, naltrexone, NSAIDs, keratolytics, antidepressants, anticonvulsants, steroids, anesthetics, acid reducers, calcium channel blockers, anti-anxiety drugs, mucolytics, or antihistamines, including combinations thereof. In an above or another embodiment, the topical composition comprises an additional active selected from one or more stimulants, disinfectants, nerve depressants, muscle relaxants, NMDA (N-Methyl-D-aspartate) receptor antagonists, opiate or opioid agonists, and/or other active agents.

In some examples, the one or more additional active drugs include an antimicrobial agent comprising one or more antimicrobial drugs.

In one example, the topical treatment comprises antimicrobial agent powder mixed with statin powder. In a further example, the topical treatment also includes naltrexone powder. In another example, the topical treatment comprises antimicrobial agent powder in a separate pharmaceutical container or container for further compounding with the statin powder and/or one or more base components to formulate a compounded premix or administration composition. In some embodiments, all or a portion of the antimicrobial agent is provided in a separate second composition comprising a solution, lotion, paste, cream, ointment, emulsion, or gel for co-administration as described herein. Thus, various embodiments of the examples and embodiments of the compositions described above and elsewhere herein comprising one or more statins may further comprise one or more antimicrobial drugs or may be provided in separate compositions for co-administration with an additional composition comprising one or more antimicrobial drugs. Example antimicrobial drugs include antibacterial drugs, antifungal drugs, and viral drugs, or combinations thereof.

The topical treatment may include a topical composition including a statin component comprising one or more statins in a dosage amount described above or elsewhere herein, such as between about 5 mg and about 200 mg, alone or including an additional active agent comprising naltrexone and/or an antimicrobial agent comprising one or more antimicrobial drugs described herein. The topical composition may be formulated for administration to wounds, necrotic tissue, broken tissue, unbroken tissue, or other targeted areas of the body, that may or may not be infected or having bacterial, fungal, or other causative organisms present. The target tissue may include skin, nails, mucosal surfaces, and potentially internalized infections, e.g., via transdermal administration of antimicrobial agents. The topical composition may be formulated to treat wounds or damaged tissue, including broken and/or unbroken skin. The topical composition may further be formulated to treat neurological pain and/or muscle pain. In some embodiments, the topical composition may treat pain accompanying diseases and conditions, such as diabetic neuropathy, radiculopathy, or shingles. The topical composition may be formulated to treat inflammation caused by arthritis or gout, for example. The topical composition may be formulated to assist in debridement of wounds. In some embodiments, the topical composition may further comprise an additional active selected from one or more NSAIDs, keratolytics, antidepressants, anticonvulsants, steroids, anesthetics, acid reducers, calcium channel blockers, antianxiety drugs, mucolytics, or antihistamines, including combinations thereof. In an above or another embodiment, the topical composition comprises an additional active selected from one or more stimulants, disinfectants, nerve depressants, muscle relaxants, NMDA (N-Methyl-D-aspartate) receptor antagonists, opiate or opioid agonists, and/or other active agents.

In various embodiments, the topical composition comprises one or more statins and an antimicrobial agent comprising or consisting of one or more antifungal drugs selected from one or more categories of antifungals including azoles (imidazoles), antimetabolites, allylamines, morpholine, glucan synthesis inhibitors (echinocandins), polyenes, benoxaborale; other antifungal/onychomycosis agents, and new classes of antifungal/onychomycosis agents. For example, the antifungal may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antifungal is selected from one or more azoles. In one embodiment, the antifungal is selected from itraconazole, voriconazole, or combination thereof. The antifungal agent or antifungal drugs thereof, may be present in a dosage amount between 25 mg and 2 gm, such as between about 25 mg and about 1800 mg, about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg, about 500 mg and about 2 gm, about 800 mg and about 1800 mg, about 500 mg and about 1500 mg, about 500 mg and about 1200 mg, about 500 mg and about 1 gm, about 500 mg and about 800 mg, about 800 mg and about 1 gm, about 1 gm and about 2 gm, about 1 gm and about 1500 mg, about 1 gm and about 1200 mg, about 1200 mg and about 1500 mg, or about 1500 mg and about 2 gm, such as greater than about 25 mg, greater than about 50 mg, greater than about 100 mg, greater than about 150 mg, greater than about 200 mg, greater than about 250 mg, greater than about 350 mg, greater than about 500 mg, greater than about 700 mg, greater than about 1000 mg, greater than about 1200 mg, greater than about 1500 mg, less than about 1800 mg, less than about 1500 mg, less than about 1200 mg, less than about 1 g, less than about 800 mg, less than about 500 mg, less than about 300 mg, less than about 200 mg, less than about 150 mg, less than about 100 mg, less than about 50 mg, or less than about 35 mg. The statin component may comprise a statin selected from atorvastatin, fluvastatin, lovastatin, pitavastatin, pravastatin, rosuvastatin, simvastatin or combination thereof in an amount between about 5 mg and about 200 mg, including any range therebetween. In a further embodiment, the topical composition further includes naltrexone. In any of the above embodiments or another embodiment, the topical composition comprises one or more additional active agents described herein, such as one or more NSAIDs, keratolytics, statins, antidepressants, anticonvulsants, steroids, anesthetics, acid reducers, calcium channel blockers, antianxiety drugs, mucolytics, or antihistamines, stimulants, disinfectants, nerve depressants, muscle relaxants, NMDA (N-Methyl-D-aspartate) receptor antagonists, opiate or opioid agonists, or combination thereof.

In various embodiments, the topical composition includes an antimicrobial agent comprising or consisting of one or more antibiotic drugs selected from penicillins, cephalosporins, fluoroquinolones, aminoglycosides, monobactams, carbapenems, macrolides, other antibacterials, or combination thereof. For example, the topical composition may include one or more antibiotic drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In various embodiments, the topical composition includes an antimicrobial agent comprising or consisting of one or more antibacterials drugs selected from vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim, or combinations thereof. In one example, the topical composition comprises linezolid, levofloxacin, ciprofloxacin, or combination thereof. In some embodiments, the one or more antibacterial drugs are selected from amoxicillin, ampicillin, azithromycin, cefaclor, cefadroxil, cefazolin, cefepime, cefixime, cefpodoxime, cefprozil, ceftriaxone, cefuroxime, ceftazidime, ciprofloxacin, clarithromycin, clindamycin, colistimethate, doxycycline, erythromycin, gentamicin, isoniazid, levofloxacin, linezolid, ofloxacin, nafcillin, nitrofurantoin, mupirocin, tobramycin, vancomycin, and combinations thereof. The one or more antimicrobial drugs may be present in a dosage amount between 25 mg and 2 gm, such as between about 25 mg and about 1800 mg, about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg, about 500 mg and about 2 gm, about 800 mg and about 1800 mg, about 500 mg and about 1500 mg, about 500 mg and about 1200 mg, about 500 mg and about 1 gm, about 500 mg and about 800 mg, about 800 mg and about 1 gm, about 1 gm and about 2 gm, about 1 gm and about 1500 mg, about 1 gm and about 1200 mg, about 1200 mg and about 1500 mg, or about 1500 mg and about 2 gm, such as greater than about 25 mg, greater than about 50 mg, greater than about 100 mg, greater than about 150 mg, greater than about 200 mg, greater than about 250 mg, greater than about 350 mg, greater than about 500 mg, greater than about 700 mg, greater than about 1000 mg, greater than about 1200 mg, greater than about 1500 mg, less than about 1800 mg, less than about 1500 mg, less than about 1200 mg, less than about 1 g, less than about 800 mg, less than about 500 mg, less than about 300 mg, less than about 200 mg, less than about 150 mg, less than about 100 mg, less than about 50 mg, or less than about 35 mg. The statin component may comprise a statin selected from atorvastatin, fluvastatin, lovastatin, pitavastatin, pravastatin, rosuvastatin, simvastatin or combination thereof in an amount between about 5 mg and about 200 mg, including any range therebetween. In a further embodiment, the topical composition further includes naltrexone. In any of the above embodiments or another embodiment, the topical composition comprises one or more additional active agents described herein, such as one or more NSAIDs, keratolytics, statins, antidepressants, anticonvulsants, steroids, anesthetics, acid reducers, calcium channel blockers, antianxiety drugs, mucolytics, or antihistamines, stimulants, disinfectants, nerve depressants, muscle relaxants, NMDA (N-Methyl-D-aspartate) receptor antagonists, opiate or opioid agonists, or combination thereof.

In various embodiments, the antimicrobial agent comprises or consists of one or more antiviral drugs selected from acyclovir, famciclovir, valacyclovir, and combinations thereof, in a dosage amount between 25 mg and 2 gm, such as between about 25 mg and about 1800 mg, about 25 mg and about 900 mg, about 25 mg and about 500 mg, about 25 mg and about 200 mg, about 50 mg and about 1 gm, about 50 mg and about 800 mg, about 50 mg and about 500 mg, about 50 mg and about 200 mg, about 100 mg and about 1 gm, about 100 mg and about 800 mg, about 100 mg and about 500 mg, about 300 mg and about 1 gm, about 300 mg and about 800 mg, about 300 mg and about 500 mg, about 500 mg and about 2 gm, about 800 mg and about 1800 mg, about 500 mg and about 1500 mg, about 500 mg and about 1200 mg, about 500 mg and about 1 gm, about 500 mg and about 800 mg, about 800 mg and about 1 gm, about 1 gm and about 2 gm, about 1 gm and about 1500 mg, about 1 gm and about 1200 mg, about 1200 mg and about 1500 mg, or about 1500 mg and about 2 gm, such as greater than about 25 mg, greater than about 50 mg, greater than about 100 mg, greater than about 150 mg, greater than about 200 mg, greater than about 250 mg, greater than about 350 mg, greater than about 500 mg, greater than about 700 mg, greater than about 1000 mg, greater than about 1200 mg, greater than about 1500 mg, less than about 1800 mg, less than about 1500 mg, less than about 1200 mg, less than about 1 g, less than about 800 mg, less than about 500 mg, less than about 300 mg, less than about 200 mg, less than about 150 mg, less than about 100 mg, less than about 50 mg, or less than about 35 mg. The statin component may comprise a statin selected from atorvastatin, fluvastatin, lovastatin, pitavastatin, pravastatin, rosuvastatin, simvastatin or combination thereof in an amount between about 5 mg and about 200 mg, including any range therebetween. In a further embodiment, the topical composition further includes naltrexone. In any of the above embodiments or another embodiment, the topical composition comprises one or more additional active agents described herein, such as one or more NSAIDs, keratolytics, statins, antidepressants, anticonvulsants, steroids, anesthetics, acid reducers, calcium channel blockers, antianxiety drugs, mucolytics, or antihistamines, stimulants, disinfectants, nerve depressants, muscle relaxants, NMDA (N-Methyl-D-aspartate) receptor antagonists, opiate or opioid agonists, or combination thereof.

In one example, the additional active component includes one or more antimicrobial drugs comprising a quinolone. Quinolones utilize a mechanism of action that includes inhibition of DNA replication and transcription. In various embodiments, the additional active component comprises one or more quinolone selected from one or more first generation quinolones such as nalidixic acid, oxolinic acid, cinoxacin, piromidic acid, pipemidic acid, or flumequine; one or more second generation quinolones such as ciprofloxacin, enoxacin, fleroxacin, levofloxacin, lomefloxacin, norfloxacin, ofloxacin, pefloxacin, rufloxacin; one or more third generation quinolones such as gatifloxacin, grepafloxacin, pazufloxacin, sparfloxacin, temafloxacin, or tosufloxacin; or one or more fourth generation quinolones such as clinafloxacin, gemifloxacin, moxifloxacin, sitafloxacin, or trovafloxacin; or combinations thereof. In one embodiment, the quinolone is selected from ciprofloxacin, levofloxacin, moxifloxacin, ofloxacin, or combination thereof. In one embodiment, the additional active component comprises ciprofloxacin, levofloxacin, or both. In an example, the additional active component comprises levofloxacin in a dosage amount between about 100 mg and about 1000 mg, such as about 125 mg, about 500 mg, or about 750 mg. In some arrangements, levofloxacin may be utilized from a contained powder comprising bulk powder or ground tablet powder or solution, for example, together with statin component or separate for co-administration therewith as described herein, which may include further combining with base component.

In one example, the additional active component includes an antimicrobial drug comprising mupirocin. In one example, mupirocin is administered in a mupirocin ointment, such as a commercially available 2% mupirocin ointment; mupirocin cream, such as a commercially available 2% mupirocin cream; bulk powder; or ground oral tablet or ground powder thereof, together with all or a portion of the statin component or co-administered therewith as described here.

In one example, the additional active component includes an antimicrobial drug comprising vancomycin. In an example, vancomycin is provided in a dosage amount between about 10 mg and about 100 mg, such as about 100 mg, which may include a contained powder, together with statin component or separate for co-administration therewith as described herein, which may include further combining with base component.

In one example, the additional active component includes an antimicrobial drug comprising one or more aminoglycosides, such as tobramycin, gentamicin, streptomycin, or combination thereof. Tobramycin may be particularly effective against gram-negative bacteria, including numerous Pseudomonas species as well as certain gram-positive bacteria including Staphylococcus aureus. Gentamicin may be particularly effective against gram-positive bacteria, including MRSA, and gram-negative bacteria, including certain Pseudomonas species. Streptomycin may be particularly effective against gram-positive and gram-negative bacteria, including *E. coli, Enterococcus,* and *Proteus.* In an example, tobramycin may be provided as a contained powder, solution, or otherwise. The contained powder may comprise powder utilized from tobramycin powder for injection. The powders may be contained or contained in pharmaceutical containers other than capsules. The tobramycin may be present together with statin component or separate for co-administration therewith as described herein, which may include further combining with base component. In an example, streptomycin may be provided as a contained bulk powder, a vial powder or solution (e.g., utilized from powder or solution for injection), or otherwise together with statin component or separate for co-administration therewith as described herein, which may include further combining with base component. In an example, gentamicin may be provided in a dosage amount between about 10 mg and about 150 mg, such as about 80 mg together with statin component or separate for co-administration therewith as described herein, which may include further combining with base component.

In one example, the additional active component includes an antimicrobial drug comprising one or more tetracyclines, such as doxycycline, tetracycline, or both. Tetracyclines inhibit bacterial protein biosynthesis by binding reversibly to the bacterial subunit 30s of the bacterial ribosome thereby inhibiting translocation of peptidyl transfer RNA. In an example, tetracycline may be provided as a contained powder bulk powder or otherwise in a dosage amount between about 100 mg and about 1000 mg, such as about 200 mg or about 500 mg, together with statin component or separate for co-administration therewith as described herein, which may include further combining with base component. In an example, doxycycline may be provided as a contained powder bulk powder or otherwise in a dosage amount between about 10 mg and about 300 mg, such as about 100 mg or 200 mg, together with statin component or separate for co-administration therewith as described herein, which may include further combining with base component.

In one example, the additional active component includes an antimicrobial drug comprising one or more macrolides, such as azithromycin. Macrolides inhibit bacterial protein biosynthesis by binding reversibly to the bacterial subunit 50s of the bacterial ribosome thereby inhibiting translocation of peptidyl transfer RNA. In an example, azithromycin may be provided as a contained powder bulk powder or otherwise in a dosage amount between about 10 mg and about 300 mg, such as about 100 mg, together with statin component or separate for co-administration therewith as described herein, which may include further combining with base component.

In one example, the additional active component includes an antimicrobial drug comprising one or more lincosamides, such as clindamycin. Lincosamides inhibit bacterial protein biosynthesis by binding reversibly to the bacterial subunit 50s of the bacterial ribosome thereby inhibiting translocation of peptidyl transfer RNA. In an example, the additional active component comprises clindamycin in a dosage amount between about 10 mg and about 500 mg, such as about 50 mg or about 300 mg. In some arrangements, clindamycin may be utilized from a bulk powder, ground tablet powder, or solution together with statin component or separate for co-administration therewith as described herein, which may include further combining with base component.

In one example, the additional active component includes an antimicrobial drug comprising one or more penicillins/cephalosporins, which inhibit formation of peptidoglycan cross-links in bacterial cell walls. Example, penicillins include piperacillin-tazobactam, ampicillin, or both. Example cephalosporins may include first generation cephalosporins, such as cephalexin, second-generation cephalosporins such as cefoxitin, third-generation cephalosporins such as ceftriaxone, fourth-generation cephalosporins such as cefepime, or combinations thereof.

In one example, the additional active component includes an antimicrobial drug comprising one or more polymyxins, which penetrate into and disrupt bacterial cell membranes. Example polymyxins include colistimethate. In an example, the additional active component comprises colistimethate in a dosage amount between about 10 mg and about 250 mg, such as about 150 mg. In some arrangements, colistimethate may be utilized from a bulk powder, ground tablet powder, or solution together with statin component or separate for co-administration therewith as described herein, which may include further combining with base component.

In one example, the additional active component includes an antimicrobial drug comprising one or more sulfa-based subsets that act by inhibition of bacterial utilization of PABA (para-aminobenzoic acid) for the synthesis of folic acid, an important metabolite in DNA synthesis. One example is sulfamethoxazole.

In one example, the additional active component includes an antimicrobial drug comprising trimethoprim, which blocks the production of tetrahydrofolic acid from dihydrofolic acid by binding to and reversibly inhibiting the required enzyme, dihydrofolate reductase. In an example, the additional active agent includes sulfamethoxazole and trimethoprim provided as a contained powder together with statin component or separate for co-administration therewith as described herein, which may include further combining with base component.

In one example, the additional active component includes an antimicrobial drug comprising one or more nitrofurans, such as nitrofurantoin, which inactivate or alter bacterial ribosomal proteins and other molecules.

In one example, the additional active component includes an antimicrobial drug comprising one or more oxazolidinone, such as linezolid, which bind to the bacterial 23S ribosomal RNA of the 50s subunit and prevent formation of a functional 70s initiation complex limiting bacterial production. In an example, the additional active component comprises linezolid in a dosage amount between about 10 mg and about 750 mg, such as about 300 mg or about 600 mg. In some arrangements, linezolid may be utilized from a bulk powder, oral tablet, or ground tablet powder, which may be contained, together with statin component or separate for co-administration therewith as described herein, which may include further combining with base component.

In one example, the additional active component includes an antimicrobial drug comprising one or more nystatin, which binds sterols in the cell membrane of susceptible species resulting in the change in membrane permeability and the subsequent leakage of intracellular components.

In one example, the additional active component includes an antimicrobial drug comprising one or more azoles, which selectively inhibit fungal cytochrome P-450 sterile C-14 alpha-demethylation. In various embodiments, the additional active component comprises one or more azoles selected from clotrimazole, ketoconazole, itraconazole, voriconazole, or combination thereof. Some embodiments may utilize other or additional azoles. In an example, the additional active component comprises voriconazole in a dosage amount between about 10 mg and about 300 mg, such as about 200 mg. In some arrangements, voriconazole may be utilized from a bulk powder, oral tablet, ground tablet powder, or solution for injection together with statin component or separate for co-administration therewith as described herein, which may include further combining with base component. In an example, the additional active component comprises fluconazole in a dosage amount between about 10 mg and about 400 mg, such as about 200 mg, which may comprise a contained bulk powder or ground oral tablet powder, together with statin component or separate for co-administration therewith as described herein, which may include further combining with base component. In an example, the additional active component comprises metronidazole in a dosage amount between about 10 mg and about 500 mg, such as about 375 mg, which may comprise a contained powder, for example, together with statin component or separate for co-administration therewith as described herein, which may include further combining with base component. In an example, the additional active component comprises clotrimazole in a dosage amount between about 5 mg and about 50 mg, such as about 20 mg, which may comprise a contained powder, for example, together with statin component or separate for co-administration therewith as described herein, which may include further combining with base component. In an example, the additional active component comprises itraconazole in a dosage amount between about 5 mg and about 80 mg, such as about 50 mg, which may comprise a contained powder, for example, together with statin component or separate for co-administration therewith as described herein, which may include further combining with base component.

In one example, the additional active component includes an antimicrobial drug comprising amphotericin in a dosage amount between about 1 mg and about 75 mg, such as about 10 mg or about 50 mg. Amphotericin binds to the sterol component of a cell membrane, leading to alterations in cell permeability and cell death. In an example, amphotericin may be provided as a contained powder or solution (e.g., utilized from a solution for injection) together with statin component or separate for co-administration therewith as described herein, which may include further combining with base component.

In one example, the additional active component comprises acyclovir. In an example, acyclovir may be provided as a contained powder or suspension together with statin component or separate for co-administration therewith as described herein, which may include further combining with base component.

In one example, the additional active component comprises a mucolytic, such as acetylcysteine in a dosage amount between about 50 mg and about 150 mg, such as about 100 mg. In an example, acetylcysteine may be provided as a contained powder together with statin component or separate for co-administration therewith as described herein, which may include further combining with base component.

In one example, the additional active component comprises an antihistamine, such as azelastine in a dosage amount between about 50 mg and about 700 mg, such as about 500 mg. In an example, azelastine may be provided as a contained powder together with statin component or separate for co-administration therewith as described herein, which may include further combining with base component.

In one example, the additional active component comprises urea in a dosage amount of between 50 mg and 1000 mg, such as about 500 mg, together with statin component or separate for co-administration therewith as described herein, which may include further combining with base component.

In one example, the additional active component comprises an NSAID, such as diclofenac, together with statin component or separate for co-administration therewith as described herein, which may include further combining with base component.

In one example, the additional active component comprises a local anesthetic, such as lidocaine, together with statin component or separate for co-administration therewith as described herein, which may include further combining with base component.

In one example, the additional active component comprises tobramycin, methylprednisolone, or both provided in a powder, cream, lotion, ointment, solution, emulsion (o/w, w/o), gel, or paste composition together with statin component or separate for co-administration therewith as described herein, which may include further combining with base component. The tobramycin may be administered in a dosage amount between about 50 mg and about 150 mg, such as about 90 mg, and the methylprednisolone may be administered in a dosage amount between about 1 mg and about 10 mg, such as about 5 mg.

Further example additional active components include (a) ciprofloxacin, mupirocin, betamethasone, and clotrimazole, (b) ciprofloxacin, betamethasone, and clotrimazole, (c) doxycycline and itraconazole (e.g., about 100 mg doxycycline and about 50 mg itraconazole), (d) doxycycline and mupirocin (e.g., about 200 mg doxycycline and about 30 mg mupirocin), (e) fluticasone (e.g., about 3 mg), (f) gentamicin, doxycycline, and mupirocin (e.g., about 160 mg gentamicin, about 100 mg doxycycline, and about 20 mg mupirocin), (g) gentamicin, mupirocin, betamethasone, and clotrimazole, (h) gentamicin, betamethasone, and clotrimazole (e.g., about 80 mg gentamicin, about 10 mg betamethasone, and about 10 mg clotrimazole), (i) gentamicin, mupirocin, and betamethasone, (j) gentamicin and methylprednisolone (e.g., about 90 mg gentamicin and about 5 mg methylprednisolone), (k) itraconazole and methylprednisolone (e.g., about 50 mg itraconazole and about 5 mg methylprednisolone), (l) levofloxacin, clindamycin, and itraconazole (e.g., about 50 mg levofloxacin, about 25 mg clindamycin, and about 25 mg itraconazole), (m) mupirocin, fluticasone, and itraconazole (e.g., about 100 mg mupirocin, about 3 mg fluticasone, and about 50 mg itraconazole), (n) mupirocin, betamethasone, and clotrimazole, (o) mupirocin, clindamycin, and itraconazole (e.g., about 20 mg mupirocin, about 25 mg clindamycin, and about 25 mg itraconazole), (p) mupirocin and methylprednisolone (e.g., about 20 mg mupirocin and about 5 mg methylprednisolone), (q) mupirocin and itraconazole (e.g., about 20 mg mupirocin and about 50 mg itraconazole), (r) tobramycin, doxycycline, mupirocin, and itraconazole (e.g., powder or ointment), (s) theophylline (e.g., about 100 mg), (t) tobramycin and fluticasone (e.g., about 100 mg tobramycin and about 1 mg fluticasone), (u) tobramycin and methylprednisolone (e.g., about 90 mg tobramycin and about 5 mg methylprednisolone), (v) diclofenac, lidocaine, and prilocaine (e.g., a cream), fluticasone, amitriptyline, and gabapentin (e.g., a cream), (w) diclofenac and lidocaine (e.g., a solution), (x) fluocinonide cream (e.g., 0.1% cream), (y) acetic acid and hydrocortisone, and (z) betamethasone. Still additional examples include one or more of budesonide, cefepime, ceftriaxone, clobetasol, fluocinolone, ipratropium, meropenem (e.g., between about 750 mg and about 1250 mg), nitrofurantoin (e.g., between about 10 mg and about 35 mg), paromomycin (e.g., between about 150 mg and about 300 mg), piperacillin-tazobactam, collagenase (e.g., collagenase ointment), or combinations thereof.

In one example, the additional active component comprises collagenase. In one formulation, the topical treatment comprises collagenase powder mixed with statin powder. In another example, the topical treatment comprises collagenase powder in a separate pharmaceutical container or container for further compounding with statin powder and/or one or more base components to formulate a compounded premix or administration composition. In some embodiments, all or a portion of the collagenase is provided in a separate second composition comprising a solution, lotion, paste, cream, ointment, emulsion, or gel for co-administration as described herein. Thus, various embodiments of the examples and embodiments of the compositions described above and elsewhere herein comprising one or more statins may further comprise collagenase or may be provided in separate compositions for co-administration with an additional composition comprising collagenase. The collagenase may be present in an amount equivalent to between about 75 and about 1250 units. In some embodiments, a pharmaceutical container according to the present description may contain collagenase in a dosage amount between about 500 units and about 750 units.

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more antidepressants selected from doxepin, nortriptyline, tetracycline, amitriptyline, and combinations thereof.

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more nonsteroidal anti-inflammatory drug (NSAID) selected from oxicams, such as meloxicam or piroxicam; salicylic acid derivatives, such as aspirin, diflunisal, salsalate, or trilisate; propionic acids, such as flurbiprofen, ibuprofen, ketoprofen, naproxen, or oxaprozin; acetic acids, such as diclofenac, etodolac, indomethacin, ketorolac, nabumetone, sulindac, or tolmetin; fenamates, such as meclofenamate; and/or COX-2 inhibitors, such as celecoxib, rofecoxib, or valdecoxib.

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more local anesthetics selected from lidocaine, prilocaine, benzocaine, or combination thereof.

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more steroids including a corticosteroid selected from amcinonide, betamethasone dipropionate, betamethasone valerate, clobetasol propionate, desoximetasone, diflorasone diacetate, flurandrenolide, fluticasone propionate, fluocinonide, halcinonide, halobetasol propionate, mometasone furoate, triamcinolone acetonide, or combination thereof.

In one embodiment, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more antianxiety drugs (e.g., buspirone), calcium channel blockers (e.g., amlodipine), and/or antihistamines (e.g., azelastine).

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises a keratolytic agent selected from urea, salicylic acid, papain, or combinations thereof.

In one example, the topical composition comprising a statin component may include one or more statins selected from atorvastatin, fluvastatin, lovastatin, pitavastatin, pravastatin, rosuvastatin, simvastatin or combination thereof in an amount between about 5 mg and about 200 mg, including any range therebetween. In a further example, the topical composition further includes naltrexone in an amount between about 1 mg and about 50 mg, including any range therebetween. In any of the above examples or another example, the topical composition comprises one or more muscle relaxants selected from baclofen, carisoprodol, chlorzoxazone, cyclobenzaprine, dantrolene, diazepam, metaxalone, methocarbamol, orphenadrine, quinine sulfate, tizanidine, and/or other muscle relaxants.

In an above or another example, the additional active component comprises one or more antimicrobial drugs, such as those described herein. For example, an embodiment of each of the above example statin components may be combined with or co-administered with one or more antifungal drugs selected from amphotericin b, ciclopirox, clotrimazole, econazole, fluconazole, itraconazole, ketoconazole, miconazole, nystatin, oxiconazole, tolnaftate, voriconazole, or a combination thereof. In another example, an embodiment of each of the above example statin components may be combined with or co-administered with one or more antibacterial drugs selected from vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim. In another example, one or more antifungal drugs selected from fluconazole, itraconazole, voriconazole, amphotericin, nystatin, clotrimazole, terconazole, ketoconazole, or combination thereof and one or more antibacterial drugs are selected from vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim, or combination thereof. Example dosage amounts of antifungal drugs and antibacterial drugs may be between 0.5 mg and 1.5 g. For example, dosage amounts tobramycin in an amount between about 10 mg and about 1.2 g, colistimethate in an amount between about 50 g and about 300 g, voriconazole in an amount between about 50 mg and about 500 mg, clotrimazole in an amount between about 10 mg and about 150 mg, ceftriaxone in an amount between about 100 mg and about 1 g, gentamicin in an amount between about 10 mg and about 200 mg, levofloxacin in an amount between about 100 mg and about 1 g, or mupirocin in an amount between about 5 mg and about 100 mg. Some embodiments may include higher or lower dosage amounts for the above antimicrobial drugs.

An embodiment of each of the above examples may comprise a base component including xylitol, poloxamers, or both. In one example, the topical composition comprising statin includes LoxaSperse™.

An embodiment of each of the above examples may include a base component comprising an ointment, liquid, or powder carrier as described herein for topical administration in an ointment, spray, bath, irrigation, or powder. Alternatively, an embodiment of each of the above examples may include a base component comprising a water washable, moisturizing ointment comprising polyethylene glycol, meadowsweet extract, zinc acetate, and propylene glycol. In one embodiment, the polyethylene glycol comprises PEG-8 and PEG-75. Alternatively, an embodiment of each of the above examples includes a base component or is combined with a base component comprising petrolatum. Alternatively, an embodiment of each of the above examples includes a base component or is combined with a base component comprising a cream base or cream type base. For example powder components of a pharmaceutical composition including the statin component alone or together with one or more antimicrobial agents, naltrexone, or one or more additional active agents, may be combined with a base component to formulate a cream or ointment, which may comprise a water washable ointment.

In any of the above examples, the statin component may comprise a statin in a dosage amount described herein. For example, the statin component may comprise one or more statins in an amount between about 5 mg and about 200 mg. In various embodiments, atorvastatin may be present in a dosage amount between about 5 mg and about 200 mg, such as between about 10 mg and about 80 mg, about 60 mg and about 150 mg, or about 90 mg and about 180 mg, fluvastatin may be present in a dosage amount between about 5 mg and about 200 mg, such as between about 20 mg and about 80 mg, lovastatin in a dosage amount between about 5 mg and about 200 mg, such as between about 10 and about 60 mg, about 60 mg and about 150 mg, or about 90 mg and about 180 mg, pitavastatin in a dosage amount between about 5 mg and about 200 mg, such as about 60 mg and about 150 mg, or about 90 mg and about 180 mg, pravastatin in a dosage amount between about 5 mg and about 200 mg, such as between about 10 mg and about 80 mg, about 60 mg and about 150 mg, or about 90 mg and about 180 mg, rosuvastatin in a dosage amount between about 5 mg and about 200 mg, such as between about 5 mg and about 40 mg, about 60 mg and about 150 mg, or about 90 mg and about 180 mg, simvastatin in a dosage amount between about 5 mg and about 200 mg, such as between about 5 mg and about 80 mg, about 60 mg and about 150 mg, or about 90 mg and about 180 mg. In another embodiment, pitavastatin is present in a dosage amount between about 1 mg and about 4 mg.

In various embodiments, the additional active component comprises a commercially available medicated composition including all or a portion of the additional active component. For example, the medicated composition may be co-administered with a statin containing composition or statin may be compounded with the medicated composition.

Various embodiments of the topical treatment include a statin component, such as an above example statin component, and an additional active component either together in a combination composition or co-administered in one or more separate compositions. In one example, the additional active component comprises collagenase. The collagenase may be provided in an ointment, solution, powder, cream, lotion, gel, or paste format. In one application, the collagenase is provided in a commercially available medicated composition such as collagenase ointment marketed under the name Santyl™ by Smith & Nephew, Inc., Fort Worth, TX 76109 including white petroleum. The statin component may be combined with the collagenase ointment to formulate an administration composition or may be co-administered separately. For example, the statin component may be administered to a body surface in a solution (e.g., footbath, bath, soak, irrigation), ointment, or powder before or after co-administration of the collagenase ointment to the same body surface.

In various embodiments, a method of compounding may comprise addition of an active component comprising the one or more statin powders to a base component wherein the base component comprises one or more base components including a liquid, semi-liquid, or solid carrier. For example, the base component may include an aqueous, organic, or inorganic solution, which may include a dispersion or suspension, cream, gel, ointment, lotion, emulsion, powder, or paste.

A method of compounding a composition including the statin component may comprise containing one or more statins powders. In one example, all or a portion of the one or more statins that are contained comprise ground oral statin tablets. In a further example, the method may include grinding one or more oral tablets comprising a statin prior to containing the resulting powder. In some embodiments, the method may also include containing one or more antimicrobial powders as described herein together with or separate of all or a portion of the powder including the one or more statins. For example, the method may include containing antifungal and/or antibacterial powder with the statin powder or in a separate pharmaceutical container. Pharmaceutical containers may include single or multiple dosages for combining with one or more base components. In one embodiment, pharmaceutical containers include a base component powder and the contents of the pharmaceutical container may be applied directly to a wound, necrotic tissue, broken tissue, unbroken tissue, or other targeted areas of the body, that may or may not be infected or may be further combined with additional base component, which may be same or different from the contained portion of the base component, prior to topical administration at the target tissue. In one embodiment, the method may include supplying or enclosing the dry powder in pharmaceutical containers other containers in addition to or instead of capsules. For example, all or some of the powder may be enclosed in pharmaceutical containers comprising a packet, satchel, vial, or powder pouch. In one embodiment, all or a portion of the statin component is provided in a first composition formulated and is co-administered with a second composition comprising all or a portion of the additional active component. In one example, the first composition comprises a powder, solution, or ointment and the second composition comprises a commercially available medicated composition. In one example, the additional active component comprises one or more antimicrobial drug, collagenase, or a combination thereof.

In an above or another method, compounding a composition including statin component comprises combining the contained or contained powder comprising the one or more statins with a base component to formulate a topical composition comprising statin for topical administration to a wound, necrotic tissue, broken tissue, unbroken tissue, or other targeted areas of the body, that may or may not be infected or a premix for further mixing with another or additional base component. For example, a capsule may be opened, broken, or dissolved to release the contained powder. In embodiments wherein one or more additional active and/or base components, such as antimicrobials, xylitol, poloxamers, or combinations thereof, are not contained or may be contained separately from the one or more statins, the method may further include addition of such ingredients. One or more additional ingredients may also be included in a premix or may be added prior to, during, or after further addition of additional base component to the premix. In one instance, one or more additional actives or base components may comprise a format other than powder, e.g., solution, suspension, gel, ointment, cream, lotion, or paste. In some embodiments, premix composition may comprise a powder, solution, suspension, gel, ointment, cream, lotion, or paste format suitable for further mixing with base component to formulate a composition for topical administration to a wound, necrotic tissue, broken tissue, unbroken tissue, or other targeted areas of the body, that may or may not be infected, in an ointment, powder, liquid spray, bath, or irrigation. One or more additional ingredients may be included in the premix or may be added prior to, during, or after further addition of base component to the premix. In one embodiment, all or a portion of the statin component is provided in a first composition formulated from the premix and that is co-administered with a second composition comprising all or a portion of the additional active component. In one example, the first composition comprises a powder, solution, or ointment and the second composition comprises a commercially available medicated composition. In one example, the additional active component comprises one or more antimicrobial drug, collagenase, or a combination thereof.

In one embodiment, a method of compounding a composition including statin component comprises combining one or more oral statin tablets and a base component to formulate a composition for topical administration or a premix for further mixing with another or additional base. The oral statin tablets may be ground to a fine powder and added to the base component may comprise a powder, liquid, emulsion, or ointment carrier/diluent, for example. In some embodiments, the powder may be dissolved in a solvent, suspended in solution, or wetted with a base component prior to combining with all or a portion of a remainder of base component. Solvent, suspending, or wetting agents may include alcohols, water, DMSO, or other suitable agents. In embodiments including additional ingredients, such as antimicrobials and/or base components comprising xylitol, poloxamers, or combinations thereof, the method may include further combining such ingredients with the remainder of the active component and base component. One or more of the additional ingredients may comprise a format other than powder, e.g., solution, suspension, gel, ointment, cream, lotion, or paste. Compositions comprising a premix may comprise a powder, solution, suspension, gel, ointment, cream, lotion, or paste format suitable for further mixing with base to formulate a composition for topical administration to a wound, necrotic tissue, broken tissue, unbroken tissue, or other targeted areas of the body, that may or may not be infected, in an ointment, powder, liquid spray, bath, or irrigation. One or more additional ingredients, such as actives or a base component, may be included in the premix or may be added prior to, during, or after further addition of base component to the premix. In one embodiment, all or a portion of the statin component is provided in a first composition formulated from the premix and that is co-administered with a second composition comprising all or a portion of the additional active component. In one example, the first composition comprises a powder, solution, or ointment and the second composition comprises a commercially available medicated composition. In one example, the additional active component comprises one or more antimicrobial drug, collagenase, or a combination thereof.

A contained composition may include one or more statin powders together with one or more base components and/or additional active drugs. For example, the topical treatment may comprise a composition including one or more statin powders and a base component wherein the base component comprises xylitol and/or poloxamer powder. In one example, the contained powder includes one or more additional powder active drugs instead of or in addition to the xylitol and/or poloxamer powder. For example, the contained powder may include collagenase or one or more antimicrobial drugs, such as one or more antifungal drugs, antibacterial drugs, antiviral drugs, or combinations thereof. The contained powder may be applied directly to a wound, necrotic tissue, broken tissue, unbroken tissue, or other targeted areas of the body, that may or may not be infected, or may be combined with one or more additional base components, such as a carrier/diluent, prior to administration. In one embodiment, all or a portion of the contained statin component comprises a first composition that is co-administered with a second composition comprising all or a portion of the additional active component. In one example, the first composition comprises a powder, solution, or ointment and the second composition comprises a commercially available medicated composition. In one example, the additional active component comprises one or more antimicrobial drug, collagenase, or a combination thereof.

A premix may include one or more statin powders combined with and/or for further combination with, which may include additional base component. In another or further example, the premix may include all or a portion of the additional active component. For example, the premix may be further mixed with additional active drugs or base component prior to administration. In one example, a premix includes statin powders dissolved, dispersed, or suspended in a base component comprising an ointment, emulsion, or solution carrier. In another or further embodiment, the premix may include collagenase or one or more antimicrobial drugs, such as one or more antifungal drugs, antibacterial drugs, antiviral drugs, or combinations thereof or may be co-administered with a second composition including all or a portion of the additional active component. The premix may be combined with one or more additional base components, such as a carrier/diluent, prior to administration. In one embodiment, the premix may contain xylitol and/or poloxamer. In another embodiment, xylitol and/or poloxamer may be added to the premix prior to administration.

In various embodiments, a method of compounding a composition comprising the statin component comprises compounding a premix as described above and elsewhere herein for addition to a base component, which may typically comprise a carrier/diluent, to formulate a composition comprising an ointment, powder, or liquid for topical administration to a wound, necrotic tissue, broken tissue, unbroken tissue, or other targeted areas of the body, that may or may not be infected, in an ointment, powder, liquid spray, bath, or irrigation. Formulating such a composition may include combining one or more statins and one or more base components as described herein. Additional active ingredients such as collagenase or an antimicrobial agent may also be added. In some embodiments, some or all the statin and/or additional active ingredients may include pure powder formats, powder from ground oral tablets, or both. Combining may include adding all or a portion of the powder to be combined with all or a portion of base component and mixing. In some embodiments, all or a portion of the powder may be dispersed, suspended, or dissolved in a liquid to form a paste, solution, dispersion, or suspension prior to addition to the base. In one of an above or another embodiment, all or a portion of the powder may be directly added to all or a portion of base component. According to various embodiments, base component may comprise a suitable base to formulate a premix composition comprising a format selected from a cream, gel, lotion, ointment, emulsion (oil-in-water or water-in-oil), foam, solution, dispersion, or powder, for example, suitable for topical application. Base component may be present in a premix formulation in an amount sufficient to obtain a desired amount of active drugs per unit weight or volume when further mixed with additional base component, which may be a same or different base component composition. The one or more active drugs may be mixed, dispersed, suspended, solubilized, or dissolved with the base component. In some embodiments, base component may comprise suitable components to formulate a composition for topical administration comprising a format selected from a cream, gel, lotion, ointment, emulsion (oil-in-water or water-in-oil), foam, liquid, dispersion, or powder, for example, suitable for topical application that when mixed with the one or more statins, which may include a compounded premix, and additional ingredients formulates an ointment, powder, liquid spray, bath, or irrigation. In other embodiments, the composition for topical administration comprises another format such as an emulsion, cream, lotion, gel, or paste. Base component may be present in an amount sufficient to obtain the desired amount of active drugs per unit weight or volume or when further mixed with additional base component, which may be the same or different base component composition. The one or more active drugs of the active component may be mixed, dispersed, suspended, solubilized, or dissolved in base component.

In some embodiments, the methods may include combining the active drugs with base component comprising a commercially available base vehicle composition for compounding. The base vehicle composition may be liquid, semi-liquid, or solid. For example, the base vehicle composition may include an aqueous, organic, or inorganic solution, which may include a dispersion or suspension, cream, gel, ointment, lotion, emulsion, powder, or paste. Thus, the method of formulating the composition may include addition of statin powder and/or ground oral statin tablets to a topical base vehicle for compounding to formulate a composition for administration, which may include co-administration, comprising a cream, ointment, solution, powder, gel, lotion, or paste, for example. In embodiments including antimicrobial agents, the method may also include addition of antimicrobial drug powder or ground oral tablets containing antimicrobial drug to a topical base for compounding. Non-limiting examples may include Spira-Wash® Gel, Lipoderm®, Loxasperse®, Mucolox™, or Versabase® Cream, Goam, Gel, Lotion or Shampoo, manufactured and distributed by PCCA, 9901 South Wilcrest Drive, Houston, TX 77099.

A method of treating a wound, necrotic tissue, broken tissue, unbroken tissue, or other targeted areas of the body, that may or may not be infected, may comprise topically administering the topical treatment to the target tissue or adjacent tissue. The target tissue may include intact or broken skin or underlying tissue. The target tissue may include intact or broken mucosal tissue, such as of the eye, gingivae, vagina, or anus. In various embodiments, topical administration of the topical treatment may be used to treat a wound comprising severely burned tissue, a cut, inflamed skin or mucosal tissue, an ulcer, necrotic tissue, slow healing wound attendant to diabetes, post-surgical site healing, e.g., in oral cavity, bone implantation or grafting, post-hemorrhoidectomy pain, dry eye, dry or scaly skin such as that related to ichthyosis or Sjogren-Larsson Syndrome, radiation induced skin toxicity, chemotherapy induced alopecia, chronic periodontitis, psoriasis, cutaneous plaque psoriasis, acne vulgaris, or combinations thereof.

In some embodiments, a method of treatment of a wound may comprise compounding and/or dispensing a capsule or pharmaceutical container comprising one or more compositions of the topical treatment, which may comprise a contained powder, premix, or composition for administration. In one embodiment, a method of treatment of a wound may comprise administering the topical treatment described herein.

In one example, the method of treating a wound comprises treating the wound with a wound ointment according to the topical treatment described herein. The wound ointment may be applied directly to wounded skin or tissues or adjacent thereto. In various applications, the applied wound ointment may be exposed or occluded.

In one example, the method of treating a wound comprises treating the wound with a wound powder according to the topical treatment described herein. The wound powder may be applied directly to wounded skin or tissues or adjacent thereto. In various embodiments, the applied wound powder may be exposed or occluded.

In one example, the topical treatment comprises a liquid spray for administering to a wound in a spray. The wound spray may comprise an aqueous or non-aqueous base component. In some examples, the base component may comprise an aqueous liquid comprising water, sodium chloride solution, hydrogen peroxide, or sodium hypochlorite. A contained powder comprising one or more statins as described herein may be combined with the base prior to administration in a spray. The one or more statins and additional ingredients, when present, may be dispersed, suspended, solubilized, or dissolved in the base. In one example, a composition comprising a premix ointment may be added to a base to formulate a wound spray. The base may comprise an aqueous liquid comprising water, sodium chloride, hydrogen peroxide, or sodium hypochlorite. The wound spray may be sprayed onto wounded skin, tissue, or adjacent regions thereof.

Various embodiments comprising a liquid format may be administered in a footbath, which may include a hand bath or soak, for example, to treat a wound. The method may include adding the statin component to a footbath. The statin component added to the footbath may comprise a composition a described herein such as a contained powder, one or more ground oral tablets, a premix, for example, wherein base component or additional base has been added before, during, or after the statin component is added to the footbath. In some embodiments, one or more ground statin tablets may be added to base component and mixed in the footbath or in a container for further addition to the footbath. A base component comprising a carrier including an aqueous diluent may in various embodiments be in addition to a base component already present. For example, a composition comprising statin component in a solution, cream, ointment, powder, gel, paste, or lotion format may be added to a footbath. Additional base component comprising a carrier/aqueous diluent may also be added. In some embodiments, prior to addition of the diluent the statin component comprises, a concentrated powder or premix, and following addition of the carrier/diluent, the resultant composition comprises the statin dosage amounts described herein. The footbath solution may be agitated and/or heated in some embodiments. A foot or a hand may contact the footbath solution in the footbath for administration of the composition. In another embodiment, the statin component may be added to a liquid base or may include a liquid base and be formulated for irrigation treatment of a wound. In some examples, irrigation treatments may include higher doses of active drugs than identified above. For example, some topical treatment compositions for irrigation treatment may include two to three times higher dosage of active drug.

A "footbath" refers to a container that can hold some volume (e.g., about 1.0 liters to about 10 liters) of a footbath solution, which may typically be an aqueous solution or suspension, and is designed to physically accommodate at least a portion of one or both feet of a subject. A footbath administration includes administration of the topical composition utilizing a footbath. A footbath may be used as a hand bath; however, smaller bathing containers may typically be utilized as hand baths. In various embodiments, footbath solutions may be utilized as hand bath solutions. A footbath can comprise several features or agents that affect various functions. For example, a footbath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or feet of the subject, a massage agent (e.g., a roller) that provides massaging contact to at least a portion of one or both feet, a pedicure agent that can clean or contact a foot or feet with a pumice, or a combination thereof. In an aspect, a footbath can have a waterfall element. In an aspect, an agitation agent or an agitator can be coupled to both a motor and the footbath. In an aspect, a footbath can comprise one or more splashguards and other spill-resistant features to ensure that the water remains enclosed within a container. A footbath may also accommodate a subject's calves, meaning that the container is "deep" so as to allow the enclosed water to contact both the feet and at least a portion of the calves of the subject. Several manufacturers market footbaths including PIBB, Dr. Scholl's, Kendal, Conair (e.g., Model FB5X, FB3, FB27R, FB30, FB52, etc.), and Brookstone.

In one embodiment, a topical treatment kit includes the statin component described herein or one or more components thereof. For example, a kit may include one or more oral tablets of one or more statins for grinding into a fine powder for topical administration consistent to that described herein. In one example, the kit includes a pill crusher for grinding the one or more oral tablets. In another example, a kit includes one or more statin powders from bulk powder contained or otherwise contained. In a further example to an above example, the kit includes a base component. In an embodiment, the kit comprises a premix including the statin powder, bulk or ground oral statin tablets, in base component for further combining with additional or different base component. In another embodiment, the kit includes the base component and powder and/or oral tablets separate for further compounding prior to administration. In one example, the kit includes a footbath and contained statin powder and/or one or more oral statin tablets. The kit may also include all or a portion of the additional active component comprising one or more additional active drugs. For example, the kit may include one or more additional active drugs selected from antimicrobials, collagenase, NSAIDs, steroids, local anesthetics, steroids, antihistamines, or combinations thereof. Other active drugs may also be included. One or more additional active drugs may comprise a bulk powder or ground oral tablet contained with or separate from the one or more statins. In one embodiment, the kit includes one or more oral tablets comprising some or all the additional active component for grinding to a fine powder and combining with the base component and statin. In some embodiments, one or more additional active drugs may comprise a solution, emulsion, cream, ointment, gel, or lotion format for addition to the one or more statin powder and/or base component. Some embodiments may include the additional active component within a commercially available medicated composition, such as any of those described herein.

Various examples of additional active components are describes below, as well as else herein. Consistent with the present description, it will be appreciated that all or a portion of the additional active component may be provided in a composition for co-administration with another composition comprising some or all of the statin component. Further, any of the compositions may include all or a portion of the statin component and the additional active component. Thus, examples include statin component and additional active component provided in a single composition or compositions for co-administration and may include formats and be administered as described herein. Similarly, the components and compositions may comprise contained powders, solutions, ointments, premixes, or compositions for administration, as also described herein. For example, a combination composition or one or more co-administration compositions may comprise a powder, cream, lotion, ointment, solution, emulsion (o/w, w/o), gel, or paste, for example. In an particular example topical treatment including the statin component and additional active component described herein, a powder, cream, lotion, ointment, solution, emulsion (o/w, w/o), gel, or paste composition including all or a portion of the additional active component is co-administered with a powder, ointment, or solution (e.g., spray, irrigation, bath) including all or a portion of the statin component.

As introduced above, in some embodiments, the topical treatment includes one or more topical compositions including collagenase. In one example, the collagenase may be provided in a powder format. When an additional active agent is included, the additional active agent may be provided within the same or a different topical composition. In various embodiments, an additional active agent of a topical treatment includes one or more antimicrobial drugs, one or more statins, and/or naltrexone, which may be provided in the same topical composition or a different topical composition than the collagenase.

In one embodiment, the topical treatment comprises collagenase. The collagenase may be provided in a single topical composition or multiple topical compositions. In one example, the topical treatment includes a topical composition comprising collagenase. In a further example, the only active in the topical treatment is collagenase. In one embodiment, the topical composition comprises collagenase and an additional active as described herein. For example, the additional active may include one or more statins, naltrexone, an antimicrobial agent (e.g., antifungal, antibacterial, antiviral), NSAIDs, keratolytics, statins, antidepressants, anticonvulsants, steroids, anesthetics, acid reducers, calcium channel blockers, antianxiety drugs, mucolytics, or antihistamines, stimulants, disinfectants, nerve depressants, muscle relaxants, NMDA (N-Methyl-D-aspartate) receptor antagonists, opiate or opioid agonists, and/or other active agents.

In a further or another embodiment, the topical composition comprises collagenase and one or more antimicrobials. The topical treatment or topical composition thereof may be administered to a wound, necrotic tissue, broken tissue, unbroken tissue, or other targeted areas of the body, that may or may not be infected.

The collagenase may be present in an amount equivalent to between about 75 and about 1250 units. In some embodiments, a pharmaceutical container according to the present description may contain collagenase in a dosage amount between about 500 units and about 750 units.

In various embodiments, the topical treatment includes collagenase in combination with a statin selected from one of atorvastatin, fluvastatin, lovastatin, pitavastatin, pravastatin, rosuvastatin, or simvastatin. The statins may be present in an amount between about 5 mg and about 200 mg, or any other amount or range thereof identified above. In one example, the topical treatment includes collagenase in a dosage amount described above in combination with one of atorvastatin in an amount between about 10 mg and about 80 mg, fluvastatin in an amount between about 20 mg and about 80 mg, lovastatin in an amount between about 10 and about 60 mg, pitavastatin in an amount between about 1 mg and about 4 mg, pravastatin in an amount between about 10 mg and about 80 mg, rosuvastatin in an amount between about 5 mg and about 40 mg, or simvastatin in an amount between about 5 mg and about 80 mg. It is noted that the above statin ranges include all potential ranges within the upper and lower bounds. thereof; one or more antimicrobial drugs; and a base component comprising an ointment carrier, powder carrier, or liquid carrier.

In some embodiments, compositions described herein as being contained may be otherwise contained such as in a vial or pouch. As also noted above, compositions described as being contained may also include oral tablets that may be ground to a fine powder for addition to base component or administration.

Dry powder components of the present disclosure may be mixed prior to being supplied into, e.g., contained within, the pharmaceutical container or after being removed from a pharmaceutical container. The dry powder may be mixed to ensure homogeneous mixing. In one example, dry powder components may be mixed with a motorized shaker-type mixer, such as a TURBULA® mixer. Aliquots of mixed dry powders or topical compositions comprising dry powders mixed with carriers, vehicles, diluents, or other base components to generate a non-powder format, e.g., solution, paste, gel, cream, ointment, or the like, may be prepared and assayed to ensure accurate mixing and final concentration have been achieved.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a list of selectable actives, ingredients, or compositions. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a weight range is stated as 1 mg to 50 mg, it is intended that values such as 2 mg to 40 mg, 10 mg to 30 mg, 1 mg to 3 mg, or 2 mg, 25 mg, 39 mg and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of treating a wound comprising:
   administering a topical composition formulated by mixing dry powder comprising (a) 5 mg to 200 mg of one or more statins selected from atorvastatin, fluvastatin, lovastatin, pitavastatin, pravastatin, rosuvastatin or simvastatin, (b) xylitol, (c) poloxamers, (d) lactose monohydrate, (e) magnesium stearate, and (f) microcrystalline cellulose with petrolatum, a water-washable-ointment, or a cream type vehicle to a target tissue comprising a skin wound.

2. The method of claim 1, wherein the topical composition further comprises between 1 mg and 50 mg naltrexone.

3. The method of claim 1, wherein the topical composition further comprises between 1 mg and 50 mg naltrexone and an antibiotic drug or an antifungal drug.

4. The method of claim 3, wherein the topical composition comprises the water-washable-ointment, and wherein the water-washable-ointment comprises PEG-8, PEG-75, meadowsweet extract, zinc acetate, and propylene glycol.

5. The method of claim 1, wherein the topical composition further includes butylated hydroxyanisole.

6. The method of claim 1, wherein the dry powder further comprise between 1 mg and 50 mg naltrexone and/or at least one of an antibiotic drug or an antifungal drug.

7. The method of claim 1, wherein bacterial, fungal, or other causative organisms are present on the target tissue.

8. The method of claim 1, wherein bacterial, fungal, or other causative organisms are not present on the target tissue.

* * * * *